(12) United States Patent
Yang et al.

(10) Patent No.: US 11,208,418 B2
(45) Date of Patent: *Dec. 28, 2021

(54) NITROGENOUS TRICYCLIC COMPOUNDS AND USES THEREOF IN MEDICINE

(71) Applicant: SUNSHINE LAKE PHARMA CO., LTD., Guangdong (CN)

(72) Inventors: Xinye Yang, Dongguan (CN); Xiaojun Wang, Dongguan (CN); Junwen Wu, Dongguan (CN); Hong Chen, Dongguan (CN); Shengtian Cao, Dongguan (CN); Yingjun Zhang, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/962,080

(22) PCT Filed: Jan. 28, 2019

(86) PCT No.: PCT/CN2019/073303
§ 371 (c)(1),
(2) Date: Jul. 14, 2020

(87) PCT Pub. No.: WO2019/149158
PCT Pub. Date: Aug. 8, 2019

(65) Prior Publication Data
US 2020/0392146 A1 Dec. 17, 2020

(30) Foreign Application Priority Data
Feb. 2, 2018 (CN) .......................... 201810107007.1

(51) Int. Cl.
| | | |
|---|---|---|
| *C07D 491/044* | (2006.01) | |
| *C07D 491/147* | (2006.01) | |
| *C07D 498/14* | (2006.01) | |
| *C07D 471/04* | (2006.01) | |
| *C07D 491/056* | (2006.01) | |
| *A61K 31/554* | (2006.01) | |
| *A61K 31/55* | (2006.01) | |
| *A61K 31/519* | (2006.01) | |

(52) U.S. Cl.
CPC ................................ *C07D 491/044* (2013.01)

(58) Field of Classification Search
CPC ............ C07D 491/044; C07D 491/147; C07D 498/14; C07D 471/04; C07D 491/056; A61K 31/554; A61K 31/55; A61K 31/519; A61P 9/10; A61P 15/10; A61P 7/02

See application file for complete search history.

(56) References Cited

U.S. PATENT DOCUMENTS

| | | |
|---|---|---|
| 6,602,898 B1 | 8/2003 | Jinno et al. |
| 6,639,078 B1 | 10/2003 | Haffner et al. |
| 6,700,013 B2 | 3/2004 | Jinno et al. |
| 6,974,830 B2 | 12/2005 | Bauer et al. |
| 6,984,650 B2 | 1/2006 | Haffner et al. |
| 7,034,046 B2 | 4/2006 | Bauer et al. |
| 7,098,336 B2 | 8/2006 | Bauer et al. |
| 7,319,109 B2 | 1/2008 | Boggs et al. |
| 7,410,997 B2 | 8/2008 | Jinno et al. |
| 7,705,028 B2 | 4/2010 | Caldwell et al. |
| 7,863,302 B2 | 1/2011 | Bell et al. |
| 7,960,552 B2 | 6/2011 | Bass, III et al. |
| 8,106,077 B2 | 1/2012 | Bell et al. |
| 8,153,624 B2 | 4/2012 | Genin et al. |
| 8,158,665 B2 | 4/2012 | Caldwell et al. |
| 8,193,192 B2 | 6/2012 | Kremoser et al. |
| 8,952,042 B2 | 2/2015 | Kremoser et al. |
| 9,139,539 B2 | 9/2015 | Kinzel et al. |
| 9,150,568 B2 | 10/2015 | Tully et al. |
| 9,539,244 B2 | 1/2017 | Kinzel et al. |
| 9,751,874 B2 | 9/2017 | Gege et al. |
| 9,820,979 B2 | 11/2017 | Kinzel et al. |
| 9,932,332 B2 | 4/2018 | Gege |
| 9,938,278 B2 | 4/2018 | Gege et al. |
| 10,080,741 B2 | 9/2018 | Or et al. |
| 10,080,742 B2 | 9/2018 | Or et al. |
| 10,080,743 B2 | 9/2018 | Or et al. |
| 10,183,917 B2 | 1/2019 | Wang et al. |

(Continued)

FOREIGN PATENT DOCUMENTS

| | | |
|---|---|---|
| CN | 104045635 A | 9/2014 |
| CN | 104513213 A | 4/2015 |

(Continued)

OTHER PUBLICATIONS

Apr. 29, 2019 International Search Report issued in International Patent Application No. PCT/CN2019/073303.

(Continued)

*Primary Examiner* — Bruck Kifle
(74) *Attorney, Agent, or Firm* — Oliff PLC

(57) ABSTRACT

Nitrogenous tricyclic compounds and uses thereof in medicine, in particular, a novel nitrogenous tricyclic compound used as an FXR active regulator and a stereoisomer, a geometrical isomer, a tautomer, a N-oxide, a hydrate, a solvate, a metabolite, a pharmaceutically acceptable salt or a prodrug thereof, and use of the compound in the manufacture of a drug for treating a disease and/or disorder regulated by FXR. A pharmaceutically acceptable composition containing the compound and a method of treating a disease and/or disorder mediated by FXR comprising administering the compound or pharmaceutical composition thereof.

10 Claims, No Drawings

(56) References Cited

U.S. PATENT DOCUMENTS

| | | |
|---|---|---|
| 10,562,910 B2 | 2/2020 | Wang et al. |
| 10,689,391 B2 | 6/2020 | Or et al. |
| 2008/0096921 A1 | 4/2008 | Navas et al. |
| 2010/0120775 A1 | 5/2010 | Bass, III et al. |
| 2010/0184809 A1 | 7/2010 | Kremoser et al. |
| 2010/0249179 A1 | 9/2010 | Deaton et al. |
| 2011/0034507 A1 | 2/2011 | Akwabi-Ameyaw et al. |
| 2013/0261108 A1 | 10/2013 | Tully et al. |
| 2014/0039007 A1 | 2/2014 | Tully et al. |
| 2015/0366856 A1 | 12/2015 | Tully et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0355693 A1 | 12/2017 | Blomgren et al. |
| 2017/0368038 A1 | 12/2017 | Badman et al. |
| 2018/0099957 A1 | 4/2018 | Ma et al. |
| 2018/0141941 A1 | 5/2018 | He et al. |
| 2018/0200243 A1 | 7/2018 | Kinzel et al. |
| 2019/0127358 A1 | 5/2019 | Yoon et al. |
| 2020/0115349 A1 | 4/2020 | Kang et al. |
| 2020/0190074 A1 | 6/2020 | He et al. |

FOREIGN PATENT DOCUMENTS

| | | |
|---|---|---|
| CN | 105884758 A | 8/2016 |
| CN | 106146483 A | 11/2016 |
| CN | 106632294 A | 5/2017 |
| CN | 107021957 A | 8/2017 |
| CN | 107021958 A | 8/2017 |
| CN | 107686486 A | 2/2018 |
| CN | 108218852 A | 6/2018 |
| CN | 108264506 A | 7/2018 |
| CN | 108341822 A | 7/2018 |
| CN | 109320509 A | 2/2019 |
| CN | 109320517 A | 2/2019 |
| JP | 2007-230909 A | 9/2007 |
| WO | 2009/149795 A2 | 12/2009 |
| WO | 2017/118294 A1 | 7/2017 |
| WO | 2017/128896 A1 | 8/2017 |
| WO | 2017/133521 A1 | 8/2017 |
| WO | 2017/147047 A1 | 8/2017 |
| WO | 2018/039384 A1 | 3/2018 |
| WO | 2018/039386 A1 | 3/2018 |
| WO | 2018/059314 A1 | 4/2018 |
| WO | 2018/075207 A1 | 4/2018 |
| WO | 2018/085148 A1 | 5/2018 |
| WO | 2018/133730 A1 | 7/2018 |
| WO | 2019/007418 A1 | 1/2019 |
| WO | 2019/055808 A1 | 3/2019 |
| WO | 2019/089664 A1 | 5/2019 |
| WO | 2019/089665 A1 | 5/2019 |
| WO | 2019/089670 A1 | 5/2019 |
| WO | 2019/120088 A1 | 6/2019 |

OTHER PUBLICATIONS

Apr. 29, 2019 Written Opinion issued in International Patent Application No. PCT/CN2019/073303.

NITROGENOUS TRICYCLIC COMPOUNDS AND USES THEREOF IN MEDICINE

CROSS-REFERENCE TO RELATED APPLICATION

This application claims priority to Chinese Patent Serial No. 201810107007.1, filed with the State Intellectual Property Office of China on Feb. 2, 2018, which is hereby incorporated by reference in its entirety.

FIELD OF THE INVENTION

The present invention relates to nitrogenous tricyclic compounds combined with FXR and used as FXR regulators and pharmaceutical compositions thereof, and use of the compound and the composition in the manufacture of a medicament for treating a disease and/or disorder mediated by FXR.

BACKGROUND OF THE INVENTION

Farnesoid X receptor (FXR) is a member of the nuclear hormone receptor superfamily, which is mainly expressed in liver, kidney and intestine (Seol et al. Mol. Endocrinol (1995), 9:72-85; Forman et al. *Cell* (1995), 81:687-693). It acts in a form of a heterodimer with retinoic acid X receptor (RXR), and regulates gene transcription by binding to response elements of target gene promoters. The FXR-RXR heterodimer binds to the reverse repeat-1 (IR-1) response element with the highest affinity, in which the hexamer binding to the consensus receptor is separated by one nucleotide. FXR is a part of the correlated process, FXR is activated by bile acid (end product of cholesterol metabolism) (Makishima et al, *Science* (1999), 284: 1362-1365; Parks et al, *Science* (1999), 284:1365-1368; Wang et al, *Mol. Cell.* (1999), 3:543-553), and the bile acid was used to inhibit the catabolism of cholesterol. (Urizar et al, (2000) *J. Biol. Chem.* 275:39313-393170).

FXR is a key regulator of cholesterol homeostasis, triglyceride synthesis and fat production (Crawley, *Expert Opinion Ther. Patents* (2010), 20:1047-1057). In addition to dyslipidemia, obesity, vitamin D-related diseases, intestinal diseases, drug-induced side effects and hepatitis (Crawley, *Expert Opinion Ther. Patents* (2010), 20:1047-1057), FXR-related indications also include hepatobiliary diseases, chronic hepatitis, non-alcoholic fatty liver disease (NAFLD), non-alcoholic steatohepatitis (NASH), cholestasis, liver fibrosis, cirrhosis, and hepatitis B, metabolic diseases, lipid metabolic diseases, carbohydrate metabolic diseases, cardiovascular metabolic diseases, atherosclerosis, type II diabetes mellitus and diabetic complications (Frank G. Schaap, et al., Journal of Medicinal Chemistry, (2005), 48:5383-5402).

Small molecular compounds acting as FXR regulators have been published in the following publications: WO2000/037077, WO2003/015771, WO2004/048349, WO2007/076260, WO2007/092751, WO2007/140174, WO2007/140183, WO2008/051942, WO2008/157270, WO2009/005998, WO2009/012125, WO2009/149795, WO2008/025539, WO2008/025540, WO2012/087520, WO2012/087521, WO2012/087519, WO2013/007387 and WO2015/036442. R. C. Buijsman et al. reviewed more small molecule FXR regulators (R. C. Buijsman et al., Curr. Med. Chem. 2005, 12, 1017-1075).

Although the development of FXR regulators has made some progress, there is still a huge space for improvement. The purpose of the present invention is to provide a novel class of nitrogenous tricyclic compounds as FXR regulators, which have better biological activity and pharmacokinetic properties than the known FXR regulators.

SUMMARY OF THE INVENTION

The invention provides a compound, or a pharmaceutical composition thereof, which binds to FXR (or NR1H4 receptor) and acts as a regulator of FXR (or NR1H4 receptor). The present invention further relates to the compound or use thereof in the manufacture of a medicament for treating a disorder and/or disease by combining the compound with an FXR nuclear receptor. The present invention further describes the synthetic method of the compound. The compound of the invention shows improved bioactivity and advantages of pharmacokinetic properties.

Specifically:

In one aspect, provided herein is a compound having Formula (I) or a stereoisomer, a geometric isomer, a tautomer, an N-oxide, a hydrate, a solvate, a metabolite, a pharmaceutically acceptable salt or a prodrug thereof,

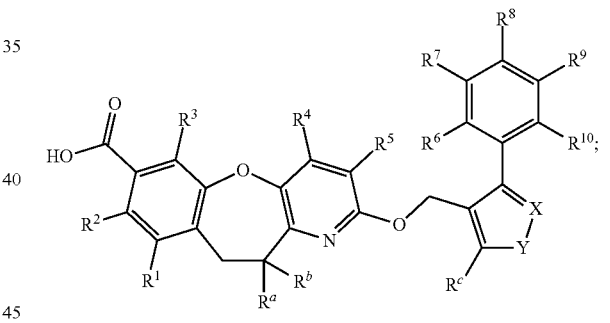

wherein

X is N or CH;

Y is O, S or NH;

each $R^a$ and $R^b$ is independently $C_{1-6}$ alkyl, $C_{1-6}$ haloalkyl, $C_{1-6}$ alkoxy, $C_{1-6}$ hydroxyalkyl or $C_{1-6}$ alkoxy-$C_{1-6}$ alkyl-; or $R^a$ and $R^b$, together with the carbon atom to which they are attached, form $C_{3-8}$ cycloalkane or 3-8 membered heterocycle;

each $R^1$, $R^2$, $R^3$, $R^4$ and $R^5$ is independently H, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{1-6}$ haloalkoxy or $C_{1-6}$ alkoxy-$C_{1-6}$ alkyl;

each $R^6$, $R^7$, $R^8$, $R^9$ and $R^{16}$ is independently H, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{1-6}$ haloalkoxy or $C_{1-6}$ alkoxy-$C_{1-6}$ alkyl or $C_{3-8}$ cycloalkyl;

$R^c$ is $C_{1-4}$ alkyl or $C_{3-6}$ cycloalkyl.

With the proviso that the compound of Formula (I) is not

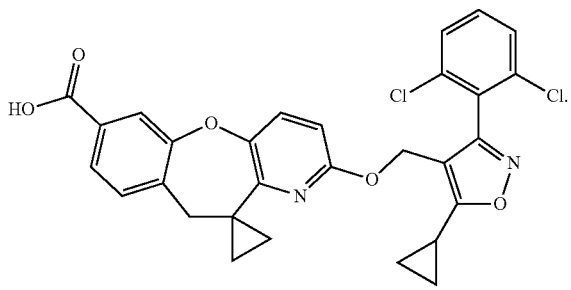 [SMILES: O=C(O)c1ccc2c(c1)Oc1ccc(OCc3c(-c4c(Cl)cccc4Cl)noc3C3CC3)nc1C1(CC1)C2]

In some embodiments, each $R^a$ and $R^b$ is independently $C_{1-3}$ alkyl, $C_{1-3}$ haloalkyl, $C_{1-3}$ alkoxy, $C_{1-3}$ hydroxyalkyl or $C_{1-3}$ alkoxy-$C_{1-3}$ alkyl-; or $R^a$ and $R^b$, together with the carbon atom to which they are attached, form $C_{3-6}$ cycloalkane or 3-6 membered heterocycle.

In other embodiments, each $R^a$ and $R^b$ is independently methyl, ethyl, n-propyl, isopropyl, difluoromethyl, trifluoromethyl, methoxy, ethoxy, n-propoxy, hydroxymethyl, 2-hydroxyethyl, 3-hydroxypropyl, methoxymethyl, ethoxymethyl, 2-methoxyethyl, 2-ethoxyethyl or 2-n-propoxyethyl; or $R^a$ and $R^b$, together with the carbon atom to which they are attached, form cyclopropane, cyclobutane, cyclopentane, cyclohexane, oxacyclopropane, trimethylene oxide or azetidine.

In some embodiments, each $R^2$, $R^3$, $R^4$ and $R^5$ is independently H, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{1-3}$ haloalkoxy or $C_{1-3}$ alkoxy-$C_{1-3}$ alkyl.

In other embodiments, each $R^2$, $R^3$, $R^4$ and $R^5$ is independently H, deuterium, F, Cl, Br, I, hydroxy, amino, nitro, cyano, methyl, ethyl, n-propyl, isopropyl, difluoromethyl, trifluoromethyl, hydroxymethyl, 1-hydroxyethyl, 2-hydroxyethyl, 3-hydroxypropyl, aminomethyl, methoxy, ethoxy, n-propoxy, methylamino, dimethylamino, trifluoromethoxy, difluoromethoxy, 2,2-difluoroethoxy, 1,2-difluoroethoxy, methoxymethyl, ethoxymethyl, 2-methoxyethyl, 2-ethoxyethyl or 2-n-propoxyethyl.

In some embodiments, each $R^6$, $R^7$, $R^8$, $R^9$ and $R^{10}$ is independently H, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{1-3}$ haloalkoxy or $C_{1-3}$ alkoxy-$C_{1-3}$ alkyl or $C_{3-6}$ cycloalkyl.

In other embodiments, each R6, R7, R8, R4 and R10 is independently H, deuterium, F, Cl, Br, I, hydroxy, amino, nitro, cyano, methyl, ethyl, n-propyl, isopropyl, difluoromethyl, trifluoromethyl, hydroxymethyl, 1-hydroxyethyl, 2-hydroxyethyl, 3-hydroxypropyl, aminomethyl, methoxy, ethoxy, n-propoxy, methylamino, dimethylamino, trifluoromethoxy, difluoromethoxy, 2,2-difluoroethoxy, 1,2-difluoroethoxy, methoxymethyl, ethoxymethyl, 2-methoxyethyl, 2-ethoxyethyl, 2-n-propoxyethyl, cyclopropyl, cyclobutyl, cyclopentyl or cyclohexyl.

In some embodiments, $R^c$ is methyl, ethyl, n-propyl, isopropyl, t-butyl, cyclopropyl, cyclobutyl, cyclopentyl or cyclohexyl.

In one aspect, provided herein is a pharmaceutical composition comprising a compound of Formula (I) disclosed herein or a stereoisomer, a geometric isomer, a tautomer, an N-oxide, a hydrate, a solvate, a metabolite, a pharmaceutically acceptable salt or a prodrug thereof, or a pharmaceutically acceptable carrier, excipient, diluent, adjuvant, vehicle or a combination thereof.

In one aspect, provided herein is use of the compound of Formula (I) or the pharmaceutical composition thereof in the manufacture of a medicament for preventing, managing, treating or lessening a disorder or disease mediated by FXR.

In some embodiments, the disease mediated by FXR is a cardiovascular disease, a disease related to dyslipidemia, obesity, metabolic syndrome, a hyperproliferative disease, fibrosis, an inflammatory disease or a disease related to liver and gallbladder.

In some embodiments, the cardiovascular disease comprises atherosclerosis, acute myocardial infarction, venous occlusive disease, portal hypertension, pulmonary hypertension, heart failure, peripheral arterial occlusive disease, sexual dysfunction, stroke or thrombosis;

wherein the obesity and the metabolic syndrome comprise insulin resistance, hyperglycemia, hyperinsulinemia, elevated levels of fatty acids or glycerol in the blood, hyperlipidemia, obesity, hypertriglyceridemia, hypercholesterolemia, syndrome X, diabetic complications, atherosclerosis, hypertension, acute anemia, neutropenia, dyslipidemia, type II diabetes, diabetic nephropathy, diabetic neuropathy, diabetic retinopathy, complications of dyslipidemia or diabetes and abnormally high body mass index;

wherein the hyperproliferative disease comprises hepatocellular carcinoma, colon adenoma, polyposis, colon adenocarcinoma, breast cancer, membranous adenocarcinoma, Bartlett's esophageal cancer and other forms of gastrointestinal or liver neoplasms;

wherein the fibrosis, the inflammatory disease and the disease related to liver and gallbladdercomprise non-alcoholic fatty liver, non-alcoholic steatohepatitis, cholestasis, hepatic fibrosis, primary biliary cirrhosis, primary sclerotic cholangitis, progressive familial intrahepatic cholestasis, cystic fibrosis, drug-induced bile duct injury, gallstone, cirrhosis, hepatitis B, sebaceous gland disease, alcoholic-induced cirrhosis, biliary obstruction, cholelithiasis, colitis, neonatal xanthosis, prevention of riboflavia or small intestinal bacterial overgrowth.

In one aspect, provided herein is a method of preventing, managing, treating or lessening a disease mediated by FXR comprising administering to a patient a therapeutic effective amount of the compound or the pharmaceutical composition of the invention.

In one aspect, provided herein is the compound or the pharmaceutical composition of the invention for use in preventing, managing, treating or lessening a disease mediated by FXR in a patient.

In a further aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and the Handbook of Chemistry and Physics, 75 th Ed. 1994. Additionally, general principles of organic chemistry are described in Sorrell et al., "Organic Chemistry", University Science Books, Sausalito: 1999, and "March's Advanced Organic Chemistry", by Michael B. Smith and Jerry March, John Wiley & Sons, New York: 2007, all of which are incorporated herein by reference in their entireties.

The term "comprise" is an open expression, it means comprising the contents disclosed herein, but do not exclude other contents.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents may be, but not limited to, H, F, Cl, Br, I, nitro, cyano, oxo ($=$O), hydroxy, alkyl, hydroxyalkyl, alkylamino, aminoalkyl, haloalkoxy, cycloalkyl, amino, aryl, heterocyclyl, heteroaryl, alkenyl, alkynyl, cycloalkyl-oxy, alkoxy, alkoxyalkyl, haloalkyl, —COOH, -alkylene-C($=$O)O-alkyl, -alkylene-S($=$O)$_2$-alkyl, -alkylene-S($=$O)$_2$-amino, —S($=$O)$_2$-alkyl, —S($=$O)$_2$-amino, —S($=$O)$_2$OH, —O-alkylene-C($=$O)O-alkyl, —O-alkylene-S($=$O)$_2$-alkyl, —O-alkylene-S($=$O)$_2$-amino, —O-alkyl ene-S($=$O)$_2$OH, —C($=$O)NH$_2$, —C($=$O)NH-alkyl, —C($=$O)N(alkyl)-alkyl, —C($=$O)NHS($=$O)$_2$-alkyl, —C($=$O)NHS($=$O)$_2$-amino, —C($=$O)NHS($=$O)$_2$OH, —N(haloalkyl)-alkyl, —N(alkyl)-S($=$O)$_2$-alkyl, —NHS($=$O)$_2$-alkyl, —NHS($=$O)$_2$-haloalkyl, —N(alkyl)S($=$O)$_2$-haloalkyl, —N(alkyl)S($=$O)$_2$-alkylamino, —NHC($=$O)-alkyl, —NHC($=$O)-haloalkyl, —N(alkyl)C($=$O)-haloalkyl, —N(alkyl)C($=$O)-alkylamino, —N(alkyl)C($=$O)O-alkyl, —NHC($=$O)O-alkyl, —NHC($=$O)O-haloalkyl, —N(alkyl)C($=$O)O-haloalkyl, —N(alkyl)C($=$O)O-aminoalkyl, —NHC($=$O)—NH$_2$, —NHC($=$O)NH-(alkyl), —NHC($=$O)NH(haloalkyl), —NHC($=$O)N(alkyl)-alkyl, —OC($=$O)-alkyl, —OC($=$O)-amino, —OC($=$O)-alkyl amino, —OC($=$O)-aminoalkyl, —OC($=$O)-alkoxy, —C($=$O)N(alkyl)S($=$O)$_2$-alkyl, —C($=$O)N(alkyl)S($=$O)$_2$-amino, —C($=$O)NH—S($=$O)$_2$OH, —C($=$NH)NH$_2$, —C($=$NH)NH-alkyl, —C($=$NH)N(alkyl)-alkyl, —C($=$N-alkyl)-NH$_2$, —C($=$O) NH-alkylene-S($=$O)$_2$OH, —C($=$O)NHC($=$O)OH, —C($=$O)NHC($=$O)O-alkyl, —C($=$O)N(alkyl)C($=$O)O-alkyl, —C($=$O)NH-alkylene-C($=$O)OH and —C($=$O) NH-alkylene-C($=$O)O-alkyl, and so on.

The term "alkyl" or "alkyl group" refers to a saturated linear or branched-chain monovalent hydrocarbon radical of 1 to 20 carbon atoms, or 1-10 carbon atoms, or 1-6 carbon atoms, or 1-4 carbon atoms, or 1-3 carbon atoms, or 1-2 carbon atoms, wherein the alkyl may be optionally and independently substituted with one or more substituents described herein. Some non-limiting examples of the alkyl group further include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_{3,3}$)$_3$), n-heptyl and n-octyl, etc. The term "alkyl" or the prefix "alk-" is inclusive of both straight chain and branched saturated carbon chain. The term "alkylidene" or "alkylene" used herein refers to a saturated divalent hydrocarbon group derived from a straight or branched chain saturated hydrocarbon by the removal of two hydrogen atoms. Examples of alkylene groups include, but are not limited to, methylene, ethylene, isopropylene, and the like.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp2 double bond, wherein the alkenyl radical may be optionally and independently unsubstituted or substituted with one or more substituents described herein, and includes radicals having "cis" and "trans" orientations, or alternatively, "E" and "Z" orientations. Examples of the alkenyl group include, but are not limited to, vinyl (—CH$=$CH$_2$), allyl (—CH$_2$CH$=$CH$_2$), butenyl (—CH$_2$CH$_2$CH$=$CH$_2$) and the like.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e. a carbon-carbon bond is sp triple bond, wherein the alkynyl radical may be optionally and independently substituted with one or more substituents described herein. Specific examples of the alkynyl group include, but are not limited to, ethyny (—C$\equiv$CH), propargyl (—CH$_2$C$\equiv$CH).

The term "heteroatom" refers to one or more of oxygen (O), sulfur(S), nitrogen (N), phosphorus (P) and silicon (Si), including any oxidized form of carbon (C), nitrogen (N), sulfur (S), or phosphorus (P); the primary to tertiary amines and quaternary ammonium salts form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl); or —C($=$O)— of heterocycle oxidated from —CH$_2$—.

The term "halogen" refers to F (fluorine), Cl (chlorine), Br (bromine), or I (iodine).

The term "unsaturated" refers to a moiety having one or more units of unsaturation.

The term "alkoxy" or "alkyl-oxy" refers to an alkyl group, as defined herein, attached to the other moiety of the compound molecular through an oxygen atom. In some embodiments, the alkoxy group is $C_{1-4}$ alkoxy. Some non-limiting examples of the alkoxy group include methoxy, ethoxy, propoxy and butoxy, and the like. The alkoxy group may be optionally and independently substituted with one or more substituents disclosed herein.

The term "alkoxyalkyl" refers to an alkyl group substituted with one or more alkoxy groups, wherein the alkoxy and alkyl are as defined herein. In some embodiments, the alkoxyalkyl is $C_{1-6}$alkoxy-$C_{1-6}$ alkyl. In other embodiments, the alkoxyalkyl is $C_{1-3}$alkoxy-$C_{1-3}$ alkyl. The "alkoxyalkyl" group may be optionally and independently substituted with one or more substituents disclosed herein.

The terms "haloalkyl", "haloalkenyl" or "haloalkoxy" refer to alkyl, alkenyl or alkoxy, as the case may be, substituted with one or more halogen atoms. In some embodiments, haloalkyl is halo $C_{1-6}$ alkyl. In other embodiments, haloalkyl is halo $C_{1-3}$ alkyl. In some embodiments, haloalkyl-oxy or haloalkoxy is halo $C_{1-6}$ alkyl-oxy or halo $C_{1-6}$ alkoxy. In some embodiments, haloalkyl-oxy or haloalkoxy is halo $C_{1-3}$ alkyl-oxy or halo $C_{1-3}$ alkoxy. Some non-limiting examples of such groups include trifluoromethyl, 2-chloro-vinyl, 2,2-difluoroethyl and trifluoromethoxy, and the like. And wherein optionally each of the haloalkyl, haloalkenyl or haloalkoxy may be optionally and independently substituted with one or more substituents described herein.

The term "alkylamino" refers to "N-alkylamino" and "N,N-dialkylamino" wherein amino groups are independently substituted with one alkyl radical or two alkyl radicals, respectively. In some embodiments, the alkylamino is an $C_{1-6}$ alkylamino group. In other embodiments, the alkylamino is an $C_{1-3}$ alkylamino group. Some non-limiting examples of such group include N-methylamino, N-ethylamino, N,N-dimethylamino, N,N-diethylamino, and the like. And wherein the alkylamino radical is optionally substituted with one or more substituents described herein.

The term "cycloalkyl" or "cycloalkane" refers to a monovalent or multivalent saturated ring having 3 to 12 carbon atoms as a monocyclic, bicyclic, or tricyclic ring system, but not containing an aromatic ring. In some embodiments, the cycloalkyl group contains 3 to 12 carbon atoms. In other embodiments, the cycloalkyl group contains 3 to 8 carbon atoms. In still other embodiments, the cycloalkyl group contains 3 to 6 carbon atoms. Some non-limiting examples of such group include cyclopropyl, cyclobutyl, cyclopentyl and cyclohexyl, etc. The cycloalkyl group may be optionally substituted with one or more substituents disclosed herein.

The term "cycloalkyloxy" refers to a cycloalkyl group attached to the rest of the molecule through an oxygen atom, wherein the cycloalkyl is as defined herein.

The term "cycloalkylalkyl" refers to a cycloalkyl group attached to the rest of the molecule through an alkyl group, wherein the cycloalkyl and alkyl are as defined herein.

The term "carbocyclyl", "carbocycle" or "carbocyclic ring" refers to a monovalent or multivalent, nonaromatic, saturated or partially unsaturated ring having 3 to 12 carbon atoms as a monocyclic, bicyclic or tricyclic hydrocarbon. A carbobicyclyl group includes a spiro carbobicyclyl group or a fused carbobicyclyl group. Suitable carbocyclyl groups include, but are not limited to, cycloalkyl, cycloalkenyl and cycloalkynyl. In one embodiment, the cycloalkyl group contains 3 to 8 carbon atoms. In other embodiment, the cycloalkyl group contains 3 to 6 carbon atoms. The examples of the carbocyclyl group further include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The cycloalkyl group may be optionally substituted with one or more substituents disclosed herein.

The term "heterocycle", "heterocyclyl", or "heterocyclic ring" as used interchangeably herein refers to a saturated or partially unsaturated monocyclic, bicyclic or tricyclic ring containing 3-12 ring atoms of which at least one ring atom is heteroatom, but not containing an aromatic ring. Unless specified otherwise, heterocyclyl may be carbon radical or nitrogen radical. Hetero atom has the definition described herein. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl. Some non-limiting examples of heterocyclyl wherein —$CH_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limiting examples of heterocyclyl wherein the ring sulfur atom is oxidized is sulfolanyl and 1,1-dioxo-thiomorpholinyl. The heterocyclyl group may be optionally substituted with one or more substituents disclosed herein.

The term "heterocyclylalkyl" refers to a heterocyclyl group attached to the rest of the molecule through an alkyl group, wherein the heterocyclyl and alkyl are as defined herein.

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members and that has a single point or multipoint of attachment to the rest of the molecule. The term "aryl" and "aromatic ring" can be used interchangeably herein. Examples of aryl ring may include phenyl, naphthyl and anthracene. The aryl group may be optionally and independently substituted with one or more substituents disclosed herein.

The term "arylalkyl" or "aralkyl" refers to an alkyl group substituted with one or more aryl groups, wherein the alkyl group and aryl group are as defined herein. Some non-limiting examples of the arylalkyl group include phenylmethyl, phenylethyl.

The term "heteroaryl" refers to monocyclic, bicyclic and tricyclic carbocyclic ring systems having a total of 5-12 ring members, or 5-10 ring members, or 5-6 ring members, wherein at least one ring in the system is aromatic, and in which at least one ring member is selected from heteroatom, and wherein each ring in the system contains 5-7 ring members and that has a single point or multipoint of attachment to the rest of the molecule. The term "heteroaryl" and "heteroaromatic ring" or "heteroaromatic compound" can be used interchangeably herein. The heteroaryl group is optionally substituted with one or more substituents disclosed herein. In one embodiment, 5-10 membered heteroaryl comprises 1, 2, 3 or 4 heteroatoms independently selected from O, S and N, wherein N may be oxidated.

Some non-limiting examples of the heteroaryl group include furanyl, imidazolyl (such as N-imidazolyl, 2-imidazolyl, 4-imidazolyl, 5-imidazolyl), isoxazolyl, oxazolyl (such as 2-oxazolyl, 4-oxazolyl, 5-oxazolyl), pyrrolyl (such as N-pyrrolyl, 2-pyrrolyl, 3-pyrrolyl), pyridyl, pyrimidinyl (such as 2-pyrimidinyl, 4-pyrimidinyl, 5-pyrimidinyl), pyridazinyl, thiazolyl (such as 2-thiazolyl, 4-thiazolyl, 5-thiazolyl), tetrazolyl (such as 5-tetrazolyl), triazolyl, thienyl (such as 2-thienyl, 3-thienyl), pyrazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothienyl, indolyl (such as 2-indolyl), purinyl, quinolinyl (such as 2-quinolinyl, 3-quinolinyl, 4-quinolinyl), 1,2,3,4-tetrahydroisoquinolinyl, 1,3-benzodioxolyl, indolinyl, isoquinolinyl (such as 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, and the like.

The term "aminoalkyl" refers to a $C_{1-10}$ linear or branched-chain alkyl group substituted with one or more amino groups. In some embodiments, the aminoalkyl is a $C_{1-6}$ alkyl group substituted with one or more amino groups. Some non-limiting examples of the aminoalkyl group include aminomethyl, aminoethyl, aminopropyl, aminobutyl and aminohexyl. Wherein the aminoalkyl group may be optionally substituted with one or more substituents disclosed herein.

The term "hydroxyalkyl" or "hydroxy-substituted alkyl" refers to an alkyl group substituted with one or more hydroxy groups, wherein the alkyl is as defined herein. Some non-limiting examples include hydroxymethyl, hydroxyethyl, 1,2-dihydroxyethyl, and the like.

The term "haloaryl" refers to an aryl group substituted with one or more halogen atoms, wherein the halogen and aryl groups are as defined herein. Some examples of the group include, but are not limited to, fluorophenyl, difluorophenyl, trifluorophenyl, chlorophenyl, dichlorophenyl, trichlorophenyl, bromophenyl, tribromophenyl, bibromophenyl, fluorochlorophenyl, fluorobromophenyl, chlorobromophenyl, and the like. The haloaryl group may be optionally substituted with one or more substituents disclosed herein.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. Wherein the alkylene group may be optionally substituted with one or more substitutents described herein. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. Such examples include methylene (—CH$_2$—), ethylene (—CH$_2$CH$_2$—), isopropylene (—CH(CH$_3$)CH$_2$—), and the like.

Furthermore, unless otherwise stated, the phrase "each . . . is independently" is used interchangeably with the phrase "each (of) . . . and . . . is independently". It should be understood broadly that the specific options expressed by the same symbol are independently of each other in different radicals; or the specific options expressed by the same symbol are independently of each other in same radicals.

Unless otherwise stated, structures depicted herein are also meant to include all isomeric (e.g., enantiomeric, diastereomeric, and geometric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

Unless otherwise stated, structures and the compound depicted herein are also meant to include all isomeric (e.g., enantiomeric, diastereomeric, and geometric (conformational isomerism)) forms of the structure, N-oxide, a hydrate, a solvate, a metabolite, a pharmaceutically acceptable salt or a prodrug thereof. Therefore, single stereochemical isomers, enantiomeric isomerrs, diastereomeric isomerrs, geometric isomerrs, conformational isomerrs, N-oxide, a hydrate, a solvate, a metabolite, a pharmaceutically acceptable salt or a prodrug thereof of the present compounds are within the scope disclosed herein. Additionally, unless otherwise stated, structures depicted herein are also meant to include compounds that differ only in the presence of one or more isotopically enriched atoms.

"Metabolite" depicted herein which show the similar active with compound of Formula (I) or Formula (II) in vivo or in vitro is a product produced through metabolism in the body of a specified compound or pharmaceutically acceptable salt, analogue or ramification thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley&Sons, Inc., New York, 1994. The compounds disclosed herein may contain asymmetric or chiral centers, and therefore there exist different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may induce that there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or salts obtained by using other methods recorded in the art such as ion exchange. Other pharmaceutically acceptable salts include adipate, malate, 2-hydroxypropionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N^+$ $(C_{1-4}$ alkyl$)_4$ salts. This invention also envisions quaternary ammonium salts formed from any of the compounds comprising nitrogen. Water or oil soluble or dispersable products may be obtained by such quaternization. Representative alkali or alkaline earth metal used for forming salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "hydrate" refers to the complex where the solvent molecule is water.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine.

An "ester" refers to an in vivo hydrolysable ester of a compound of Formula (I) containing hydroxy group, for example, a pharmaceutically acceptable ester which is hydrolysed in the human or animal body to produce the parent alcohol. Some non-limiting examples of in vivo hydrolysable ester forming groups for hydroxy include phosphate, acetoxymethoxy, 2,2-dimethylpropionyloxymethoxy, alkanoyl, benzoyl, phenyl acetyl, alkoxycarbonyl, dialkylcarbamoyl, N-(dialkylaminoethyl)-N-alkylcarbamoyl, and the like.

An "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic (C1-C24) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, all of which are incorporated herein by reference in their entireties.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) 9-fluorenylmethylenoxy-carbonyl (Fmoc) and the like. Similarly, a "hydroxy-protecting group" refers to a substituent of a hydroxy group that blocks or protects the hydroxy functionality. Suitable protecting groups include methyl, methoxymethyl, acetyl and silyl, and so on. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl) ethoxy-methy-1,2-(p-toluenesulfonyl) ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

The term "therapeutically effective amount" refers to an amount of the compound of Formula (I) which is sufficient to achieve the stated effect. Accordingly, a therapeutical effective amount of a compound of formula (I) used in for the treatment of a condition mediated by FXR will be an amount sufficient for the treatment of the condition mediated by FXR.

The term "dyslipidemia" used herein refers to abnormalities of lipid and lipoprotein in the blood, or abnormalities of lipid and lipoprotein levels, as well as diseases caused, aggravated or associated with such abnormalities. (seen in Dorland's Illutrated Medical Dictionary, the 29th Edition, W.B. Saunders Publishing Company, New York, N.Y.). The disease states included in the definition of dyslipidemia used herein include hyperlipidemia, hypertriglycerimia, low plasma HDL, high plasma LDL, high plasma VLDL, liver cholestasis and hypercholesterolemia.

The term "disorders associated with dyslipidemia" used herein includes but is not limited to atherosclerosis, thrombosis, coronary artery disease, stroke and hypertension. Diseases associated with dyslipidemia also include metabolic diseases such as obesity, diabetes, insulin resistance and their complications. The term "cholestasis" used herein refers to any disease in which the flow of bile from the liver is obstructed, either intrahepatic (i.e., intrahepatic) or extrahepatic (i.e., extrahepatic).

The term "liver fibrosis" as used herein includes liver fibrosis for any reason including, but not limited to, viral-induced liver fibrosis such as liver fibrosis caused by hepatitis B and hepatitis C; liver fibrosis due to contaction with alcohol (alcoholic liver disease), pharmaceutical compounds, oxidative stress, cancer radiotherapy or industrial chemicals; and liver fibrosis caused by diseases such as primary biliary cirrhosis, fatty liver, obesity, nonalcoholic steatohepatitis, cystic fibrosis, hemochromatosis and auto-immune hepatitis, and so on.

The term "nonalcoholic fatty liver (NAFLD)" used herein refers to a metabolic disease associated with insulin resistance, comprises simple fatty liver (SFL), nonalcoholic steatohepatitis (NASH), fatty hepatic fibrosis and cirrhotic.

The "FXR regulator" used herein refers to substances binding to FXR directly and regulating FXR activity, including FXR agonists, FXR partial agonists and FXR antagonists.

FXR agonists used herein refer to substances binding to FXR directly and up-regulating FXR activity.

The terms "a", "an", "the" and similar terms used in the context of the present invention (especially in the context of the claims) are to be construed to cover both the singular and plural unless otherwise indicated herein or clearly contradicted by the context.

DESCRIPTION OF COMPOUNDS OF THE INVENTION

The invention provides a compound, or a pharmaceutical composition thereof, which binds to FXR (or NR1H4 receptor) and acts as a regulator of FXR (or NR1H4 receptor). The present invention further relates to use of the compound or the composition thereof in the manufacture of a medicament for treating a disorder or disease by combining the compound with an FXR nuclear receptor. The present invention further describes the synthetic method of the compound. The compound of the invention shows improved bioactivity and advantages of pharmacokinetic properties.

In one aspect, provided herein is a compound having Formula (I) or a stereoisomer, a geometric isomer, a tautomer, an N-oxide, a hydrate, a solvate, a metabolite, a pharmaceutically acceptable salt or a prodrug thereof,

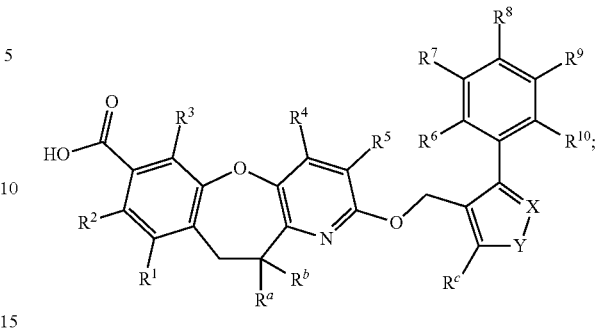

with the proviso that the compound of formula (I) is not

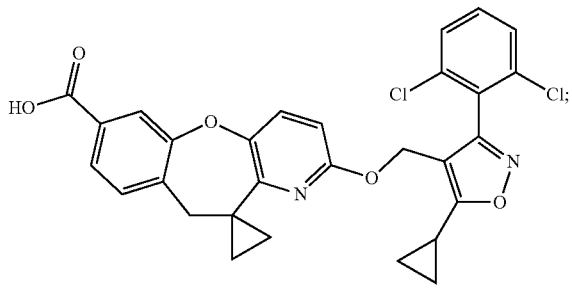

wherein X, Y, $R^a$, $R^b$, $R^c$, $R^1$, $R^2$, $R^3$, $R^4$, $R^5$, $R^6$, $R^7$, $R^8$, $R^9$ and $R^{10}$ are as defined herein.

In some embodiments, X is N or CH.

In some embodiments, Y is O, S or NH.

In some embodiments, each $R^a$ and $R^b$ is independently $C_{1-6}$ alkyl, $C_{1-6}$ haloalkyl, $C_{1-6}$ alkoxy, $C_{1-6}$ hydroxyalkyl or $C_{1-6}$ alkoxy-$C_{1-6}$ alkyl-; or $R^a$ and $R^b$, together with the carbon atom to which they are attached, form $C_{3-8}$ cycloalkane or 3-8 membered heterocycle.

In other embodiments, each $R^a$ and $R^b$ is independently $C_{1-3}$ alkyl, $C_{1-3}$ haloalkyl, $C_{1-3}$ alkoxy, $C_{1-3}$ hydroxyalkyl or $C_{1-3}$ alkoxy-$C_{1-3}$ alkyl-; or $R^a$ and $R^b$, together with the carbon atom to which they are attached, form $C_{3-6}$ cycloalkane or 3-6 membered heterocycle.

In still other embodiments, each $R^a$ and $R^b$ is independently methyl, ethyl, n-propyl, isopropyl, difluoromethyl, trifluoromethyl, methoxy, ethoxy, n-propoxy, hydroxymethyl, 2-hydroxyethyl, 3-hydroxypropyl, methoxymethyl, ethoxymethyl, 2-methoxyethyl, 2-ethoxyethyl or 2-n-propoxyethyl; or $R^a$ and $R^b$, together with the carbon atom to which they are attached, form cyclopropane, cyclobutane, cyclopentane, cyclohexane, oxacyclopropane, trimethylene oxide or azetidine.

In some embodiments, each $R^1$, $R^2$, $R^3$, $R^4$ and $R^5$ is independently H, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{1-6}$ haloalkoxy or $C_{1-6}$ alkoxy-$C_{1-6}$ alkyl.

In other embodiments, each $R^1$, $R^2$, $R^3$, $R^4$ and $R^5$ is independently H, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{1-3}$ haloalkoxy or $C_{1-3}$ alkoxy-$C_{1-3}$ alkyl.

In still other embodiments, each $R^1$, $R^2$, $R^3$, $R^4$ and $R^5$ is independently H, deuterium, F, Cl, Br, I, hydroxy, amino, nitro, cyano, methyl, ethyl, n-propyl, isopropyl, difluoromethyl, trifluoromethyl, hydroxymethyl, 1-hydroxyethyl, 2-hydroxyethyl, 3-hydroxypropyl, aminomethyl, methoxy, ethoxy, n-propoxy, methylamino, dimethylamino, trifluoromethoxy, difluoromethoxy, 2,2-difluoroethoxy, 1,2-difluoroethoxy, methoxymethyl, ethoxymethyl, 2-methoxyethyl, 2-ethoxyethyl or 2-n-propoxyethyl.

In some embodiments, each $R^6$, $R^7$, $R^8$, $R^9$ and $R^{10}$ is independently H, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{1-6}$ haloalkoxy or $C_{1-6}$ alkoxy-$C_{1-6}$ alkyl or $C_{3-8}$ cycloalkyl.

In other embodiments, each $R^6$, $R^7$, $R^8$, $R^9$ and $R^{10}$ is independently H, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{1-3}$ haloalkoxy or $C_{1-3}$ alkoxy-$C_{1-3}$ alkyl or $C_{3-6}$ cycloalkyl.

In still other embodiments, each $R^6$, $R^7$, $R^8$, $R^4$ and $R^{10}$ is independently H, deuterium, F, Cl, Br, I, hydroxy, amino, nitro, cyano, methyl, ethyl, n-propyl, isopropyl, difluoromethyl, trifluoromethyl, hydroxymethyl, 1-hydroxyethyl, 2-hydroxyethyl, 3-hydroxypropyl, aminomethyl, methoxy, ethoxy, n-propoxy, methylamino, dimethylamino, trifluoromethoxy, difluoromethoxy, 2,2-difluoroethoxy, 1,2-difluoroethoxy, methoxymethyl, ethoxymethyl, 2-methoxyethyl, 2-ethoxyethyl, 2-n-propoxyethyl, cyclopropyl, cyclobutyl, cyclopentyl or cyclohexyl.

In some embodiments, $R^c$ is $C_{1-4}$ alkyl or $C_{3-6}$ cycloalkyl.

In other aspect, provided herein is a compound having one of the following structures, or a stereoisomer, a geometric isomer, a tautomer, an N-oxide, a solvate, a hydrate, a metabolite, an ester, a pharmaceutically acceptable salt or a prodrug thereof, but not limited to these compounds:

(1)

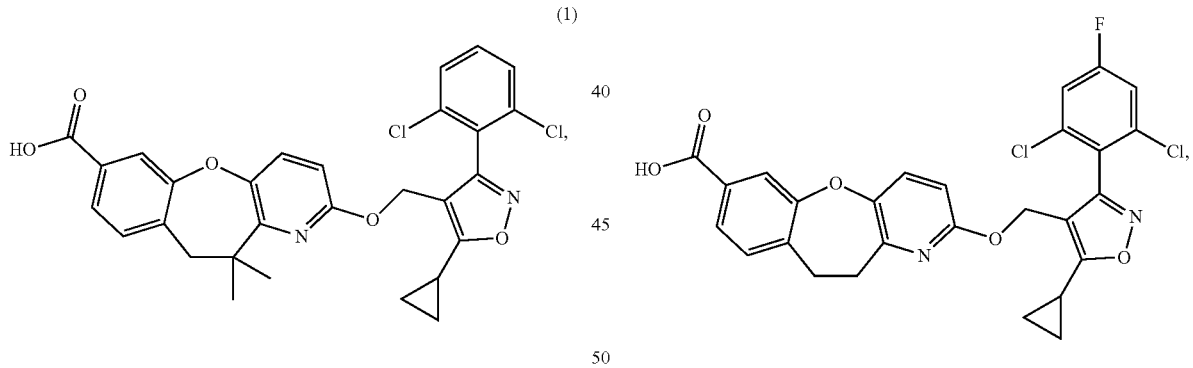

(2)

(3)

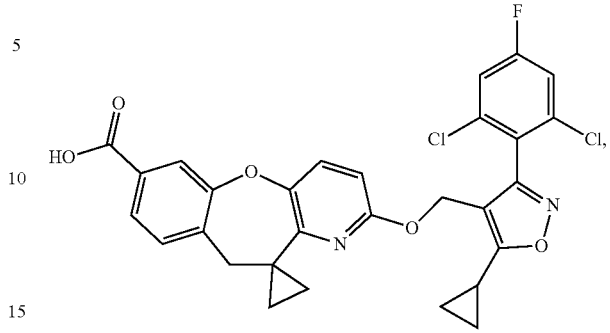

(4)

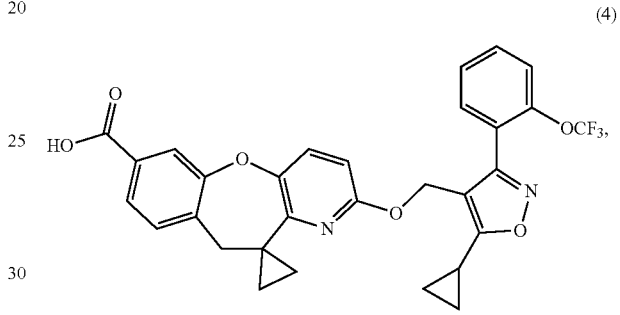

(5)

(6)

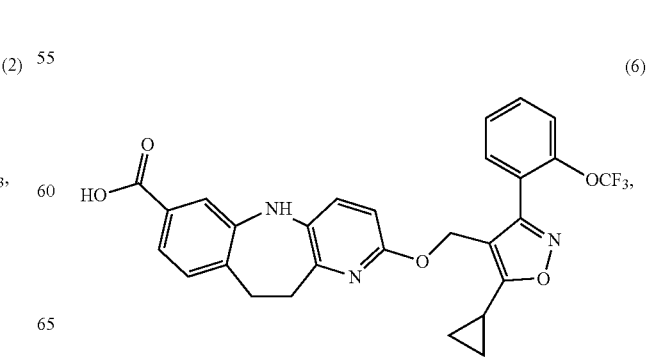

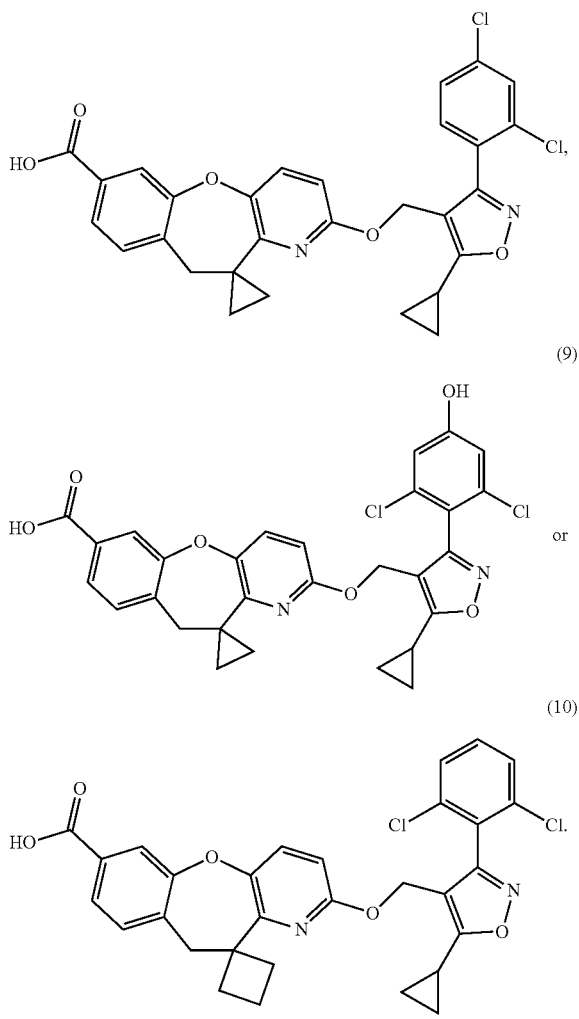

In one aspect, provided herein is a pharmaceutical composition comprising a compound of Formula (I) or a stereoisomer, a geometric isomer, a tautomer, an N-oxide, a hydrate, a solvate, a metabolite, a pharmaceutically acceptable salt or a prodrug thereof, or a pharmaceutically acceptable carrier, excipient, diluent, adjuvant, vehicle or a combination thereof.

In one aspect, provided herein is use of the compound of Formula (I) or the pharmaceutical composition thereof in the manufacture of a medicament for preventing, managing, treating or lessening a disorder or disease mediated by FXR.

In some embodiments, the disease mediated by FXR is a cardiovascular disease, a disease related to dyslipidemia, obesity, metabolic syndrome, a hyperproliferative disease, fibrosis, an inflammatory disease or a disease related to liver and gallbladder.

In some embodiments, the cardiovascular disease comprises atherosclerosis, acute myocardial infarction, venous occlusive disease, portal hypertension, pulmonary hypertension, heart failure, peripheral arterial occlusive disease (PAOD), sexual dysfunction, stroke or thrombosis.

In some embodiments, the obesity and metabolic syndrome comprise insulin resistance, hyperglycemia, hyperinsulinemia, elevated levels of fatty acids or glycerol in the blood, hyperlipidemia, obesity, hypertriglyceridemia, hypercholesterolemia, syndrome X, diabetic complications, atherosclerosis, hypertension, acute anemia, neutropenia, dyslipidemia, type II diabetes, diabetic nephropathy, diabetic neuropathy, diabetic retinopathy, complications of dyslipidemia or diabetes and abnormally high body mass index.

In some embodiments, the hyperproliferative disease comprises hepatocellular carcinoma, colon adenoma, polyposis, colon adenocarcinoma, breast cancer, membranous adenocarcinoma, Bartlett's esophageal cancer and other forms of gastrointestinal or liver neoplasms.

In some embodiments, the fibrosis, inflammatory disease and disease related to liver and gallbladder comprise non-alcoholic fatty liver (NAFLD), non-alcoholic steatohepatitis (NASH), cholestasis, hepatic fibrosis, primary biliary cirrhosis (PBC), primary sclerotic cholangitis (PSC), progressive familial intrahepatic cholestasis (PFIC), cystic fibrosis, drug-induced bile duct injury, cirrhosis, hepatitis B, sebaceous gland disease, alcoholic-induced cirrhosis, biliary obstruction, cholelithiasis, colitis, neonatal xanthosis, prevention of riboflavia or small intestinal bacterial overgrowth.

In one aspect, provided herein is the compound or the pharmaceutical composition of the invention for use in preventing, managing, treating or lessening a disease mediated by FXR in a patient.

In one aspect, the invention relates to a method for preventing, managing, treating, or lessening fibrotic diseases of tissues or organs of a patient, the method comprises administrating a therapeutically effective amount of the compound or pharmaceutical composition of the invention to the patient with FXR-mediated diseases.

The present invention relates to a method of preventing, managing, treating or lessening a disease mediated by FXR in a patient, comprising administering a therapeutically effective amount of a pharmaceutically acceptable effective amount of the compound to a patient.

In other aspect, provided herein is a method of preparing, separating or purifying the compound of Formula (I).

Pharmaceutical Composition, Formulation, Administration of the Compound of the Invention and Use of the Compound and Pharmaceutical Composition In other aspect, the characteristic of the pharmaceutical composition disclosed herein is, the pharmaceutical composition comprises the compound having Formula (I), the compound listed in the invention, or any compound of example 1-14, and a pharmaceutically acceptable carrier, excipient, or adjuvant. The amount of the compound in the composition of the invention can effectively and detectably treat or lessen a disease mediated by FXR.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As the following described: Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 19881999, Marcel Dekker, New York, both of which are herein incorporated by reference in their entireties, discloses various carriers used in formulating pharmaceutically acceptable compositions and known techniques for the preparation thereof. In addition to the scope that any conventional carrier medium is incompatible with the compounds disclosed herein, such as any undesirable biological effect produced or otherwise interaction occurring in a deleterious manner with any other components of the pharmaceutically acceptable composition, its use is contemplated to be within the scope of this invention.

The compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Ophthalmic formulations, eye ointments, powders, solutions and the like, are also contemplated as being within the scope of this invention.

The compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

When treating or preventing FXR-mediated conditions for which compounds of the present invention are indicated, generally satisfactory results are obtained when the compounds of the present invention are administered at a daily dosage of from about 0.01 milligram to about 100 milligram per kilogram of animal body weight, preferably given as a single daily dose or in divided doses two to six times a day, or in sustained release form. For most large mammals, the total daily dosage is from about 0.01 milligrams to about 1000 milligrams, preferably from about 0.1 milligram to about 50 milligrams. In the case of a 70 kg adult, the total daily dose will generally be from about 0.07 milligrams to about 350 milligrams. This dosage regimen may be adjusted to provide the optimal therapeutic response.

The compound, composition or pharmaceutically acceptable salt or hydrate thereof can be used for preventing, managing, treating or lessening a patient with a disease mediated by FXR, especially treating effectively non-alcoholic fatty liver disease (NAFLD), non-alcoholic steatohepatitis (NASH), obesity, hypertriglyceridemia, atherosclerosis, chronic intrahepatic cholestasis, primary biliary cirrhosis (PBC), primary sclerotic cholangitis (PSC), progressive familial intrahepatic cholestasis (PFIC), drug-induced bile duct injury, gallstone, cirrhosis, hepatitis B, sebaceous gland disease, alcoholic-induced cirrhosis, cystic fibrosis, biliary obstruction, cholelithiasis, liver fibrosis, dyslipidemia, atherosclerosis, type II diabetes, diabetic nephropathy, diabetic neuropathy, diabetic retinopathy, peripheral arterial occlusive disease (PAOD), colitis, neonatal xanthosis, prevention of riboflavia, venous occlusive disease, portal hypertension, metabolism syndrome, acute myocardial infarction, acute stroke, thrombosis, hypercholesterolemia, small intestinal bacterial overgrowth, erectile dysfunction, tumors of gastro-intestinal tract and tumors of liver.

General Synthetic Procedures

Generally, the compounds disclosed herein may be prepared by methods described herein, wherein the substituents are as defined as Formula (I), except where further noted. The following non-limiting schemes and examples are presented to further exemplify the invention.

One skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous CH2Cl2 and CHCl3 were obtained by refluxing the solvent with CaH2. EtOAc, PE, hexane, DMAC and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. 1H NMR spectra were recorded with a Bruker 400 MHz or 600 MHz spectrometer using $CDCl_3$, $d_6$-DMSO, $CD_3OD$ or $d_6$-acetone as solutions (reported in ppm), and using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), q (quartet), dt (doublet of triplets), tt (triplet of triplets), dddd (doublet of doublet of doublet of doublets), qd (quartet of doublets), ddd (doublet of doublet of doublets), td (triplet of doublets), dq (doublet of quartets), ddt (doublet of doublet of triplets), tdd (triplet of doublet of doublets), dtd (doublet of triplet of doublets). Coupling constants, when given, were reported in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315D DAD detector were applied in the analysis, and an ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1:

TABLE 1

The gradient elution condition of the mobile phase in Low-resolution mass spectrum analysis

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micorn, 10 min, 0.6 mL/min flow rate, 5 to 95% (0.1% formic acid in $CH_3CN$) in (0.1% formic acid in H2O). Column was operated at 40° C.

The following abbreviations are used throughout the specification:

$CDCl_3$ chloroform-d
DMF N,N-dimethylformamide
DMSO dimethylsulfoxide
DMSO-$d_6$ dimethyl sulfoxide-$d_6$
$CD_3OD$ methyl alcohol-d4
MeOH methanol
THF tetrahydrofuran
DCM dichloromethane
EA, EtOAc ethyl acetate
PE petroleum ether
Pd/C, Pd-C Palladium on activated carbon
g gram
mg milligram
$H_2O$ water
M moles per liter
mol mole
mmol millimole
mL milliliter
μL microlitre
MPa mega pascal Typical synthetic procedures for preparing the compounds of the present invention disclosed are shown in the following synthetic scheme. Unless otherwise specified, $R^1$, $R^2$, $R^3$, $R^4$, $R^5$, $R^6$, $R^7$, $R^8$, $R^9$, $R^{10}$, $R^a$, $R^b$ and $R^c$ are as defined herein.

Synthetic Methods

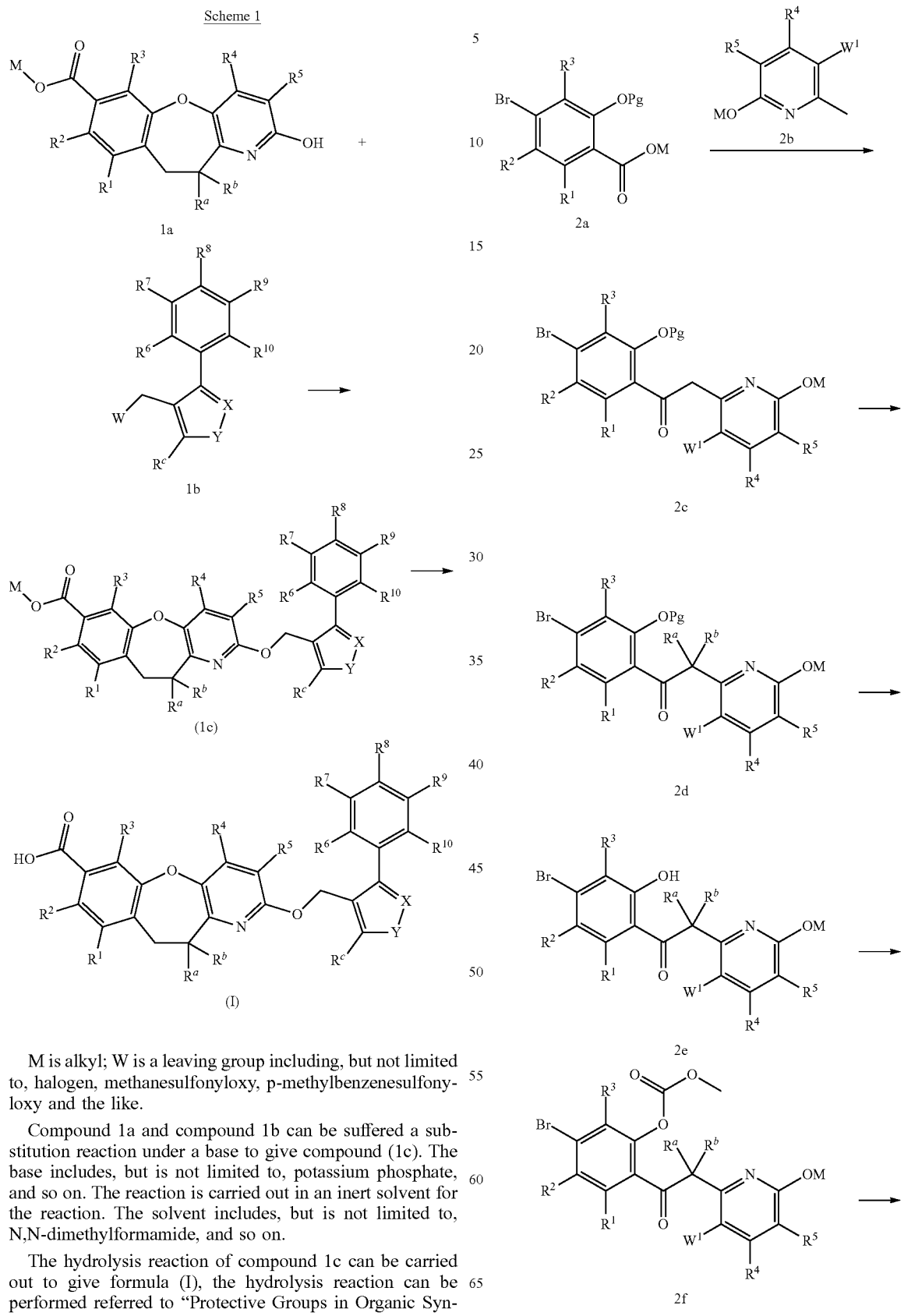

M is alkyl; W is a leaving group including, but not limited to, halogen, methanesulfonyloxy, p-methylbenzenesulfonyloxy and the like.

Compound 1a and compound 1b can be suffered a substitution reaction under a base to give compound (1c). The base includes, but is not limited to, potassium phosphate, and so on. The reaction is carried out in an inert solvent for the reaction. The solvent includes, but is not limited to, N,N-dimethylformamide, and so on.

The hydrolysis reaction of compound 1c can be carried out to give formula (I), the hydrolysis reaction can be performed referred to "Protective Groups in Organic Synthesis".

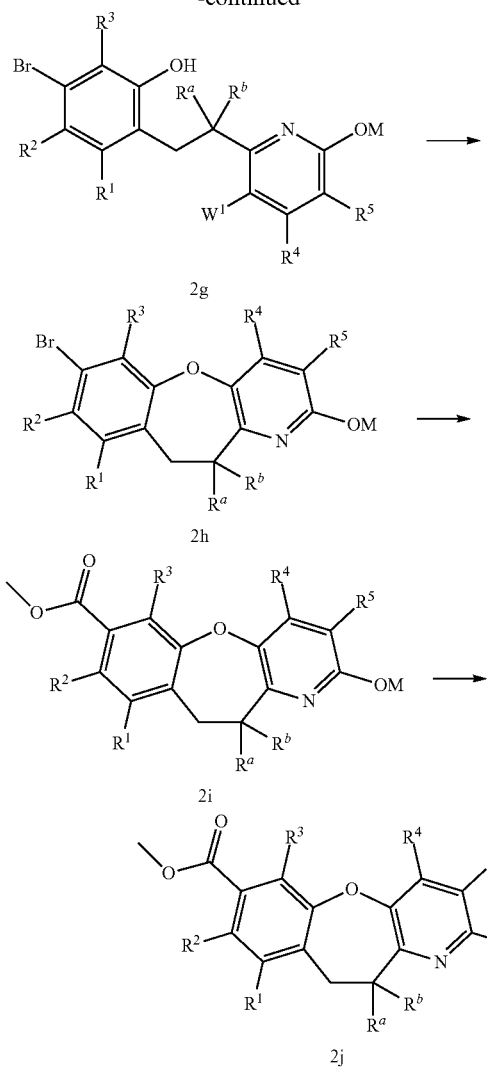

2g

2h

2i

2j

M is alkyl; Pg is the protecting group described herein; W¹ is a leaving group including, but not limited to, halogen, methanesulfonyloxy, p-methylbenzenesulfonyloxy and the like.

Compound 2a and compound 2b can be suffered a reaction under a base to give compound 2c. The base includes, but is not limited to, sodium bis(trimethylsilyl) amino, and so on. The reaction is preferably carried out in a solvent inert to the reaction, including but not limited to, tetrahydrofuran and the like.

Compound 2c and haloalkane can be suffered a substitution reaction under a base to give compound 2d. The haloalkane includes, but are not limited to, iodomethane, 1,2-dibromethane. The base includes, but is not limited to, sodium hydroxide, sodium bis(trimethylsilyl) amino, and so on. The reaction is preferably carried out in a solvent inert to the reaction, including but not limited to toluene, tetrahydrofuran and the like.

Compound 2e can be obtained from compound 2d by removing the hydroxy protecting group, the method of removing the hydroxy protecting group can refer to "Protective Groups in Organic Synthesis".

Compound 2e and methylclhlorofonmate can be suffered a reaction under a base to give active ester 2f, active ester 2f can convert to compound 2g under a reducing agent. The base includes, but is not limited to, triethylamine, and so on. The reducing agent includes, but is not limited to sodium borohydride, and so on. The reaction is carried out in a solvent inert to the reaction, including but not limited to, tetrahydrofuran and the like.

Compound 2h can be obtained from compound 2g under a catalyst and a ligand in the present of a base through a coupling reaction. The catalyst includes, but is not limited to, cuprous iodide, and so on. The ligand includes, but is not limited to, N,N-dimethylglycine, and so on. The base includes, but is not limited to, cesium carbonate, and so on. The reaction is carried out in a solvent inert to the reaction, including but not limited to, 1,4-dioxane, and the like.

Compound 2h can react with high pressure carbon monoxide gas and methanol under a palladium catalyst and a base to get compound 2i.

Compound 2j can be obtained from compound 2i by removing the hydroxy protecting group, the method of removing the hydroxy protecting group can refer to "Protective Groups in Organic Synthesis".

Scheme 3

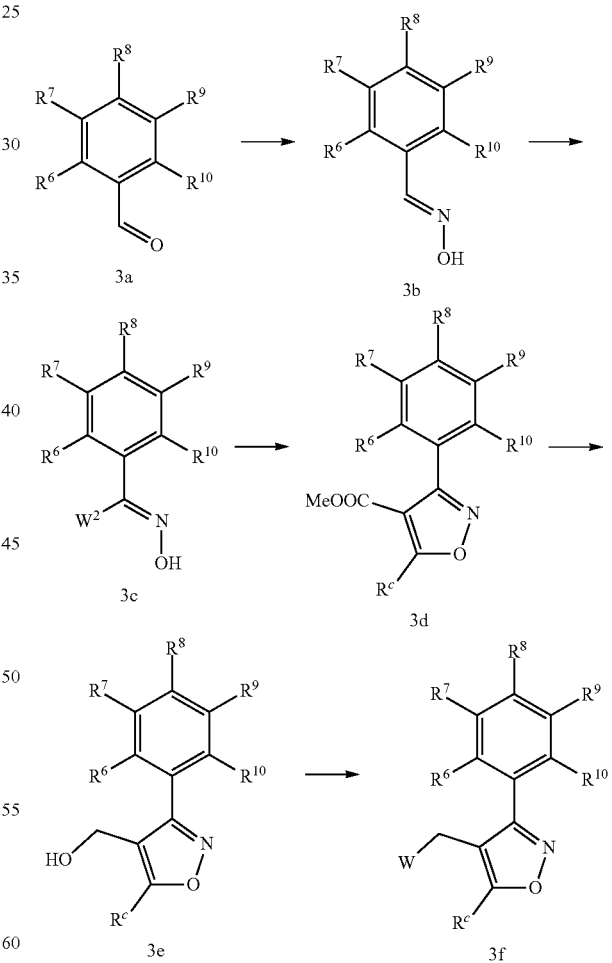

W² represents halogen atom. W is a leaving group including, but not limited to, halogen, methanesulfonyloxy, p-methylbenzenesulfonyloxy and the like.

Compound 3b can be obtained from compound 3a and hydroxylamine hydrochloride under a base by a condensation reaction. The base includes, but is not limited to, sodium hydroxide, and so on. The reaction is carried out in a solvent inert to the reaction, including but not limited to, ethanol, and the like.

Compound 3c can be obtained from compound 3b and a halogenated reagent by a halogenating reaction. The halogenated reagent includes, but is not limited to, N-chlorosuccinimide. The reaction is carried out in a solvent inert to the reaction, including but not limited to, N,N-dimethylformamide and the like.

Compound 3d can be obtained from compound 3c and methyl 3-alkyl-3-oxopropionate by a ring closure reaction under a base. The base includes, but is not limited to, potassium carbonate, and so on. The reaction is carried out in a solvent inert to the reaction, including but not limited to, tetrahydrofuran and the like.

Compound 3e can be obtained from compound 3d by a reducing reaction under a reducing reagent. The reducing agent includes, but is not limited to lithium aluminum hydride, and so on. The reaction is carried out in a solvent inert to the reaction, including but not limited to, tetrahydrofuran and the like.

Compound 3f can be obtained from compound 3e by a reaction under an activating reagent. The activating reagent includes, but is not limited to, thionyl chloride, and so on. The reaction is carried out in a solvent inert to the reaction, including but not limited to, dichloromethane and the like.

The following examples disclosed herein are presented to further describe the invention. However, these examples should not be used to limit the scope of the invention.

DETAILED DESCRIPTION OF THE EMBODIMENTS

Examples

Example 1: 2-((5-cyclopropyl-3-(2,6-dichlorophenyl)isoxazol-4-yl)methoxy)-11,11-dimethyl-10,11-dihydrobenzo[6,7]oxepino[3,2-b]pyridine-7-carboxylic acid

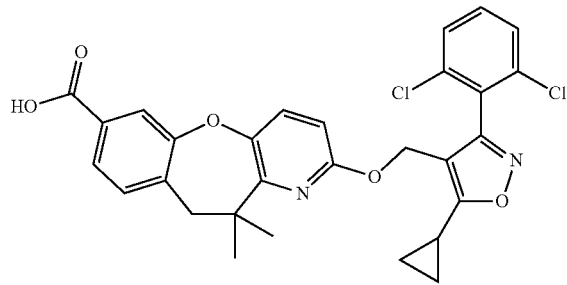 [SMILES: CC1(C)Cc2ccc(C(=O)O)cc2Oc2ccc(OCc3c(-c4c(Cl)cccc4Cl)noc3C3CC3)nc21]

Step 1: methyl 4-bromo-2-(methoxymethoxy)benzoate

Methyl 4-bromosalicylate (10 g, 43 mmol) and diisopropyl ethylamine (11.0 mL, 65 mmol) were dissolved in dichloromethane (100 mL), to the solution was added chloromethyl methyl ether (4.9 mL, 65 mmol) dropwise in an ice bath. After the addition, the mixture was stirred overnight. The reaction was quenched with water (200 mL), the resulting mixture was extracted with dichloromethane (150 mL×2). The organic layers were combined and washed with saturated brine (10 mL), dried over anhydrous sodium sulfate, filtered, and concentrated under vacuum. The residue was purified by silica gel column chromatography (PE/EtOAc (v/v)=20/1) to give the title compound as a colorless oil (10 g, 84%).

Step 2: 1-(4-bromo-2-(methoxymethoxy)phenyl)-2-(3-bromo-6-methoxypyridine-2-yl)ethanone Under nitrogen, methyl 4-bromo-2-(methoxymethoxy)benzoate (11 g, 40.0 mmol) and 3-bromo-6-methoxy-2-methyl-pyridine (8.08 g, 40.0 mmol) were dissolved in dry tetrahydrofuran (100 mL), a solution of sodium bis(trimethylsilyl)amidein tetrahydrofuran (40 mL, 80 mmol, 2.0 M) was added dropwise in an ice bath, after the addition, the mixture was warmed to rt and stirred for 3 hours. The mixture was quenched with saturated aqueous ammonium chloride (50 mL). The resulting mixture was diluted with water (100 mL) and extracted with ethyl acetate (150 mL×2). The organic layers were combined and washed with saturated brine (20 mL), dried over anhydrous sodium sulfate, filtered, and concentrated under vacuum. The residue was purified by silica gel column chromatography (PE/EtOAc (v/v)=20/1) to give the title compound as a yellow solid (11 g, 62%).

Step 3: 1-(4-bromo-2-(methoxymethoxy)phenyl)-2-(3-bromo-6-methoxypyridine-2-yl)-2-methylpropane-1-one Under nitrogen, potassium tert-butoxide (38.0 g, 339 mmol) was dissolved in tetrahydrofuran (500 mL), and then 1-(4-bromo-2-(methoxymethoxy)phenyl)-2-(3-bromo-6-methoxypyridine-2-yl)ethanone (30.0 g, 67.5 mmol) and iodomethane (27.0 mL, 434 mmol) were added at rt, the mixture was stirred at rt overnight. The mixture was filtered, the filtrate was concentrated, the residue was washed with saturated aqueous ammonium chloride (300 mL) and extracted with ethyl acetate (300 mL×2). The organic layers were combined and washed with saturated brine (50 mL), dried over anhydrous sodium sulfate, filtered, and concentrated under vacuum to give the title compound as a yellow oil (30.0 g, 94%).

Step 4: 1-(4-bromo-2-hydroxyphenyl)-2-(3-bromo-6-methoxypyridine-2-yl)-2-methylpropane-1-one 1-(4-Bromo-2-(methoxymethoxy)phenyl)-2-(3-bromo-6-methoxypyridine-2-yl)-2-methylpropane-1-one (30.0 g, 63.4 mmol) was dissolved in tetrahydrofuran (40 mL), and hydrochloric acid (6 M, 40 mL, 240 mmol) was added, after the addition, the mixture was stirred at rt for 8 hours. The reaction mixture was cooled to rt and diluted with water (30 mL), and adjusted with potassium carbonate solid to alkalinity, the resulting mixture was extracted with ethyl acetate (40 mL×2). The organic layers were combined and washed with saturated brine (10 mL), dried over anhydrous sodium sulfate, filtered, and concentrated under vacuum. The residue was purified by silica gel column chromatography (PE/EtOAc (v/v)=100/1) to give the title compound as a colorless oil (18.0 g, 66%).

MS (ESI, pos. ion) m/z: 428.0 [M+H]+.

Step 5: 5-bromo-2-(2-(3-bromo-6-methoxypyridine-2-yl)-2-methyl propionyl)phenylmethylcarbonate Under nitrogen, 1-(4-bromo-2-hydroxyphenyl)-2-(3-bromo-6-methoxypyridine-2-yl)-2-methylpropane-1-one (18.0 g, 42 mmol) was dissolved in dry tetrahydrofuran (500 mL), and triethylamine (9.0 mL, 64 mmol) and methylclhlorofonmate (4.0 mL, 52 mmol) were added dropwise in an ice bath, after the addition, the mixture was stirred in the ice bath for 6 hours. The mixture was filtered to get the title compound in tetrahydrofuran as a light yellow solution (20.0 g, 98%), which was used in the next step without further purification.

Step 6: 5-bromo-2-(2-(3-bromo-6-methoxypyridine-2-yl)-2-methylpropyl)phenol

Sodium borohydride (6.2 g, 160 mmol) was dissolved in water (200 mL), a solution of 5-bromo-2-(2-(3-bromo-6-methoxypyridine-2-yl)-2-methyl propionyl)phenylmethylcarbonate (20 g, 41 mmol) in tetrahydrofuran was added dropwise in an ice bath (400 mL), after the addition, the mixture was stirred in the ice bath overnight. The mixture was diluted with water (100 mL) and extracted with ethyl acetate (100 mL×2). The organic layers were combined and washed with saturated brine (20 mL), dried over anhydrous sodium sulfate, filtered, and concentrated under vacuum. The residue was purified by silica gel column chromatography (PE/EtOAc (v/v)=100/1) to give the title compound as a yellow oil (9.0 g, 53%).
MS (ESI, pos. ion) m/z: 414.0 [M+H]$^+$.

Step 7: 7-bromo-2-methoxy-11,11-dim ethyl-10,11-dihydrobenzo[6,7]oxepino[3,2-b]pyridine Under nitrogen, cuprous iodide (250 mg, 1.3 mmol), N,N-dimethylglycine (670 mg, 6.5 mmol), cesium carbonate (7.77 g, 23.4 mmol) and 5-bromo-2-(2-(3-bromo-6-methoxypyridine-2-yl)-2-methylpropyl)phenol (9.0 g, 21.7 mmol) were dissolved in 1,4-dioxane (150 mL), the mixture was warmed and stirred by reflux for 6 hours. The reaction mixture was cooled to room temperature and filtered, the filtrate was concentrated under vacuum. The residue was purified by silica gel column chromatography (PE/EtOAc (v/v)=100/1) to give the title compound as a white solid (2.5 g, 35%).
MS (ESI, pos. ion) m/z: 334.0 [M+H]$^+$.

Step 8: methyl 2-methoxy-11,11-dimethyl-10,11-dihydrobenzo[6,7]oxepino[3,2-b]pyridine-7-carboxylate 7-Bromo-2-methoxy-11,11-dimethyl-10,11-dihydrobenzo[6,7]oxepino[3,2-b]pyridine (0.64 g, 1.9 mmol), triethylamine (0.55 mL, 3.8 mmol) and 1,1'-bis(diphenylphosphino)ferrocene]dichloropalladium(II) (140 mg, 0.19 mmol) were dissolved in methanol (30 mL), the solution was stirred in an autoclave under carbon monoxide (3.0 MPa) at 100° C. for 2 days. The mixture was cooled to rt, and concentrated under vacuum, the residue was purified by silica gel column chromatography (PE/EtOAc (v/v)=30/1) to give the title compound as a colorless oil (200 mg, 30%).

Step 9: methyl 2-hydroxy-11,11-dimethyl-10,11-dihydrobenzo[6,7]oxepino[3,2-b]pyridine-7-carboxylate Methyl 2-methoxy-11,11-dimethyl-10,11-dihydrobenzo[6,7]oxepino[3,2-b]pyridine-7-carboxylate (200 mg, 0.64 mmol) and potassium iodide (190 mg, 1.3 mmol) were dissolved in acetonitrile (9 mL), and chlorotrimethylsilane (0.11 mL, 1.3 mmol) was added at rt, after the addition, the mixture was warmed to 85° C. and stirred for 3 hours. The mixture was cooled to rt and quenched with saturated aqueous sodium thiosulfate (50 mL). The resulting mixture was extracted with ethyl acetate (50 mL×2). The organic layers were combined and washed with saturated brine (30 mL), dried over anhydrous sodium sulfate, filtered, and concentrated under vacuum. The residue was purified by silica-gel column chromatography (DCM/MeOH=15/1, V/V) to give the title compound as a yellow solid (190 mg, 99%).
MS (ESI, pos. ion) m/z: 300.1 [M+H]$^+$.

Step 10: methyl 2-((5-cyclopropyl-3-(2,6-dichlorophenyl)isoxazol-4-yl)methoxy)-11,11-dimethyl-10,11-dihydrobenzo[6,7]oxepino[3,2-b]pyridine-7-carboxylate 4-(Chloromethyl)-5-cyclopropyl-3-(2,6-dichlorophenyl)isoxazole (290 mg, 0.95 mmol), methyl 2-hydroxy-11,11-dim ethyl-10,11-dihydrobenzo[6,7]oxepino[3,2-b]pyridine-7-carboxylate (190 mg, 0.63 mmol) and potassium phosphate (270 mg, 1.27 mmol) were dissolved in N,N-dimethylformamide (9 mL), the mixture was warmed to 50° C. and stirred for 4 hours. The reaction mixture was cooled to rt and diluted with water (10 mL), the resulting mixture was extracted with ethyl acetate (20 mL×2). The organic layers were combined and washed with saturated brine (20 mL), dried over anhydrous sodium sulfate, filtered, and concentrated under vacuum. The residue was purified by silica gel column chromatography (PE/EtOAc (v/v)=15/1) to give the title compound as a white solid (220 mg, 61%).
$^1$H NMR (400 MHz, CDCl$_3$) δ 7.81-7.76 (m, 2H), 7.37-7.32 (m, 3H), 7.31-7.29 (m, 1H), 7.27-7.24 (m, 1H), 6.33 (d, J=8.6 Hz, 1H), 5.13 (s, 2H), 3.92 (s, 3H), 3.12 (s, 2H), 2.21-2.12 (m, 1H), 1.31-1.27 (m, 8H), 1.16-1.10 (m, 2H).

Step 11: 2-((5-cyclopropyl-3-(2,6-dichlorophenyl)isoxazol-4-yl)methoxy)-11,11-dimethyl-10,11-dihydrobenzo[6,7]oxepino[3,2-b]pyridine-7-carboxylic acid Methyl 2-((5-cyclopropyl-3-(2,6-dichlorophenyl)isoxazol-4-yl)methoxy)-11,11-dimethyl-10,11-dihydrobenzo[6,7]oxepino[3,2-b]pyridine-7-carboxylate (220 mg, 0.40 mmol) was dissolved in a mixed solvent of tetrahydrofuran (12 mL) and water (12 mL), to the mixture was added sodium hydroxide (160 mg, 3.88 mmol), the resulting mixture was warmed to 80° C. and stirred for 6 hours. The reaction mixture was cooled to rt and concentrated under vacuum to remove the most solvent. The mixture was diluted with water (10 mL) and acidified with hydrochloric acid (2 M, 5 mL), and the resulting mixture was extracted with EtOAc (20 mL×2). The organic layers were combined and washed with saturated brine (10 mL), dried over anhydrous sodium sulfate, filtered, and concentrated under vacuum to give a crude product, the crude product was triturated (methyl tert-butyl ether/petroleum ether (V/V) =20/1) to give the title compound as a white solid (110 mg, 51%).
MS (ESI, pos. ion) m/z: 551.2 [M+H]$^+$;
$^1$H NMR (400 MHz, CDCl$_3$) δ 7.88-7.81 (m, 2H), 7.39-7.31 (m, 4H), 7.28-7.22 (m, 1H), 6.34 (d, J=8.6 Hz, 1H), 5.14 (s, 2H), 3.14 (s, 2H), 2.20-2.13 (m, 1H), 1.31 (s, 6H), 1.29-1.27 (m, 2H), 1.16-1.10 (m, 2H).

Example 2: 2-((5-cyclopropyl-3-(2-(trifluoromethoxy)phenyl)isoxazol-4-yl)methoxy)-10,11-dihydrobenzo[6,7]oxepino[3,2-b]pyridine-7-carboxylic acid

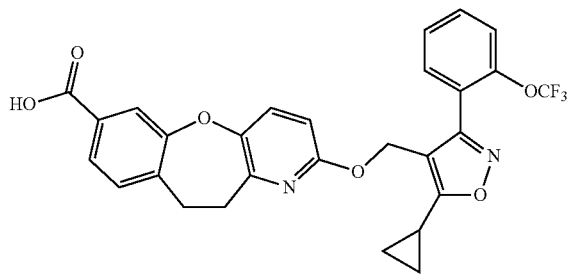 [SMILES: O=C(O)c1ccc2c(c1)Oc1ccc(OCc3c(-c4ccccc4OC(F)(F)F)noc3C3CC3)nc1CC2]

Step 1: 2-trifluoromethoxybenzaldoxime

2-Trifluoromethoxybenzaldehyde (25.0 g, 131.5 mmol) was dissolved in methanol (125 mL), and hydroxylamine hydrochloride (11.2 g, 160.5 mmol) and a solution of sodium hydroxide (6.42 g, 161 mmol) in water (60 mL) were added, the mixture was stirred at 78° C. overnight. The mixture cooled to rt and concentrated under vacuum to remove ethanol, the residue was diluted with water (200 mL), and extracted with ethyl acetate (200 mL), the organic layer was concentrated under vacuum to give the title compound as a white solid (22 g, 82%).

Step 2: 2-trifluoromethoxy-N-hydroxy-chlorobenzaldoxime

A solution of N-chlorosuccinimide (18.6 g, 139.4 mmol) in N,N-dimethylformamide (150 mL) was added into a solution of 2-trifluoromethoxybenzaldoxime (22.0 g, 107.2 mmol) in N,N-dimethylformamide (150 mL), the mixture was stirred at rt overnight. The mixture was diluted with water (1.2 L) and extracted with ethyl acetate (300 mL), the organic layer was concentrated under vacuum to give the title compound as a yellow oil (25 g, 97%).

Step 3: methyl 5-cyclopropyl-3-(2-(trifluoromethoxy)phenyl)isoxazole-4-carboxylate To a mixture of potassium carbonate (15 g, 108.5 mmol) in tetrahydrofuran (100 mL) was added a solution of methyl 3-cyclopropyl-3-oxopropionate (21 g, 147.7 mmol) in tetrahydrofuran (30 mL) in an ice bath, the mixture was stirred in the ice bath for 30 min, and then a solution of 2-trifluoromethoxy-N-hydroxy-chlorobenzaldoxime (25 g, 98.6 mmol) in tetrahydrofuran (100 mL) was added. After the addition, the mixture was stirred at rt for 77 hours. The reaction mixture was concentrated under vacuum, the residue was diluted with water (300 mL), and the resulting mixture was extracted with EtOAc (150 mL×2). The combined organic phases were dried over anhydrous sodium sulfate, filtered, and the filtrate was concentrated in vacuo. The residue was purified by silica gel chromatograph (PE/EtOAc (v/v)=200/1) to give the title compound as a red oil (32.2 g, 100%).

Step 4: (5-cyclopropyl-3-(2-(trifluoromethoxy)phenyl)isoxazol-4-yl)methanol

Under nitrogen, a mixture of lithium aluminum hydride (4.97 g, 131 mmol) in tetrahydrofuran (100 mL) was added into a solution of methyl 5-cyclopropyl-3-(2-(trifluoromethoxy)phenyl)isoxazole-4-carboxylate (39 g, 119.2 mmol) in tetrahydrofuran (100 mL) slowly in an ice bath, after the addition, the mixture was warmed to rt and stirred at rt for 50 hours. The reaction mixture was quenched with saturated aqueous ammonium chloride and diluted with water (300 mL), then concentrated hydrochloric acid (5 mL) was added, and the resulting mixture was extracted with EtOAc (150 mL×2). The combined organic layers were dried over anhydrous sodium sulfate, and filtered. The filtrate was concentrated in vacuo. The residue was purified by silica gel column chromatography (PE/EtOAc (v/v)=30/1) to give the title compound as a light red oil (1.54 g, 4.3%).
$^1$H NMR (400 MHz, CDCl$_3$) δ 7.58-7.48 (m, 2H), 7.42-7.35 (m, 2H), 4.47 (s, 2H), 2.21-2.14 (m, 1H), 1.24-1.19 (m, 2H), 1.13-1.09 (m, 2H).

Step 5: 4-(chloromethyl)-5-cyclopropyl-3-(2-(trifluoromethoxy)phenyl)isoxazole

Benzotriazole (920 mg, 7.72 mmol) was dissolved in dichloromethane (10 mL), to the solution was added thionyl chloride (0.56 mL, 7.72 mmol) dropwise under nitrogen in an ice bath, after the addition, the mixture was warmed to rt and stirred for 1.5 hours. The above reaction mixture was added into a solution of (5-cyclopropyl-3-(2-(trifluoromethoxy)phenyl)isoxazol-4-yl)methanol (1.54 g, 5.15 mmol) in dichloromethane (10 mL) dropwise under nitrogen, the resulting mixture was stirred overnight. The reaction mixture was diluted with water (100 mL), and extracted with dichloromethane (50 mL×2). The combined organic layers were dried over anhydrous sodium sulfate, and filtered. The filtrate was concentrated in vacuo. The residue was purified by silica gel column chromatography (PE/EtOAc (v/v)=50/1) to give the title compound as a red oil (900 mg, 55%).
$^1$H NMR (600 MHz, CDCl$_3$) δ 7.62-7.52 (m, 2H), 7.48-7.40 (m, 2H), 4.48 (s, 2H), 2.20-2.08 (m, 1H), 1.32-1.25 (m, 2H), 1.22-1.14 (m, 2H).

Step 6: methyl 2-((5-cyclopropyl-3-(2-(trifluoromethoxy)phenyl)isoxazol-4-yl)methoxy)-10,11-dihydrobenzo[6,7]oxepino[3,2-b]pyridine-7-carboxylate 4-(Chloromethyl)-5-cyclopropyl-3-(2-(trifluoromethoxy)phenyl)isoxazole (500 mg, 1.6 mmol), methyl 2-hydroxy-10,11-dihydrobenzo[6,7]oxepino[3,2-b]pyridine-7-carboxylate (555 mg, 2.1 mmol) (preparation method referred to step 10 of example 3 described in WO 2016127924) and potassium phosphate (1.0 g, 4.7 mmol) were dissolved in N,N-dimethylformamide (10 mL), the mixture was warmed to 60° C. and stirred for 7 hours. The reaction mixture was cooled to rt and diluted with water (200 mL), the resulting mixture was extracted with ethyl acetate (100 mL×2). The organic layers were combined and washed with saturated brine (100 mL), dried over anhydrous sodium sulfate, filtered, and concentrated under vacuum. The residue was purified by silica gel column chromatography (PE/EtOAc (v/v)=30/1) to give the title compound as a colorless oil (771 mg, 89%).
MS (ESI, pos. ion) m/z: 553.0 [M+H]$^+$.

Step 7: 2-((5-cyclopropyl-3-(2-(trifluoromethoxy) phenyl)isoxazol-4-yl)methoxy)-10,11-dihydrobenzo [6,7]oxepino[3,2-b]pyridine-7-carboxylic acid Methyl 2-((5-cyclopropyl-3-(2-(trifluoromethoxy)phenyl)isoxazol-4-yl)methoxy)-10,11-dihydrobenzo[6,7]oxepino[3,2-b]pyridine-7-carboxylate (771 mg, 1.4 mmol) was dissolved in a mixed solvent of tetrahydrofuran (15 mL) and methanol (15 mL), to the mixture was added a solution of sodium hydroxide (334 mg, 8.4 mmol) in water (15 mL), the resulting mixture was stirred at rt for 12 hours. The reaction mixture was concentrated under vacuum to remove the most solvent. The mixture was diluted with water (100 mL) and acidified with hydrochloric acid (2 M, 8 mL), and the resulting mixture was extracted with EtOAc (20 mL×2). The organic layers were combined and washed with saturated brine (10 mL), dried over anhydrous sodium sulfate, filtered, and concentrated under vacuum to give a crude product, the crude product was purified by silica gel column chromatography (dichloromethane/methanol (v/v)=200/1) to give the title compound as a white solid (530 mg, 70%).

MS (ESI, pos. ion) m/z: 539.0 [M+H]$^+$;

$^1$H NMR (400 MHz, CDCl$_3$) δ 7.91-7.79 (m, 2H), 7.59-7.53 (m, 1H), 7.53-7.46 (m, 1H), 7.42-7.30 (m, 4H), 6.42 (d, J=8.7 Hz, 1H), 5.16 (s, 2H), 3.24-3.16 (m, 2H), 3.12-3.03 (m, 2H), 2.32-2.21 (m, 1H), 1.26-1.23 (m, 2H), 1.14-1.08 (m, 2H).

Example 3: 2-((5-cyclopropyl-3-(2-(trifluoromethoxy)phenyl)isoxazol-4-yl)methoxy)-10H-Spiro[benzo[6,7]oxepino[3,2-b]pyridine-11,1'-cyclopropane]-7-carboxylic acid

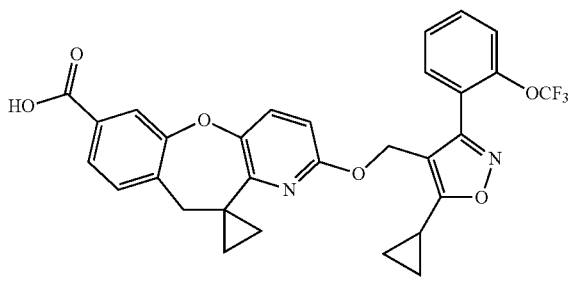 [SMILES: O=C(O)c1ccc2c(c1)Oc1ccc(OCc3c(-c4ccccc4OC(F)(F)F)noc3C3CC3)nc1C1(CC1)C2]

Step 1: (4-bromo-2-(methoxymethoxy)phenyl)(1-(3-bromo-6-methoxypyridin-2-yl)cyclopropyl)ketone Under nitrogen, 1-(4-bromo-2-(methoxymethoxy)phenyl)-2-(3-bromo-6-methoxypyridin-2-yl)ethanone (2.0 g, 4.5 mmol) was dissolved in phenyl (60 mL), to the mixture were added tetrabutylammonium hydrogen sulfate (0.15 g, 0.45 mmol) and a solution of sodium hydroxide (6.24 g, 156 mmol) in water (6 mL), and then the mixture was stirred at rt for 10 min. To the reaction mixture was added 1,2-dibromoethane (1.0 mL, 11.7 mmol) dropwise, after the addition, the mixture was stirred at rt overnight. The mixture was diluted with water (50 mL) and extracted with ethyl acetate (60 mL×2). The organic layers were combined and washed with saturated brine (20 mL), dried over anhydrous sodium sulfate, filtered, and concentrated under vacuum.

The residue was purified by silica gel column chromatography (PE/EtOAc (v/v)=30/1) to give the title compound as a yellow oil (1.9 g, 90%).

$^1$H NMR (400 MHz, CDCl$_3$) δ 7.52 (d, J=8.6 Hz, 1H), 7.33-7.25 (m, 2H), 6.98 (d, J=8.2 Hz, 1H), 6.48 (d, J=8.6 Hz, 1H), 5.13 (s, 2H), 3.94 (s, 3H), 3.49 (s, 3H), 1.92-1.87 (m, 2H), 1.65-1.61 (m, 2H).

Step 2: (4-bromo-2-hydroxyphenyl)(1-(3-bromo-6-methoxypyridin-2-yl)cyclopropyl)ketone (4-Bromo-2-(methoxymethoxy)phenyl)(1-(3-bromo-6-methoxypyridin-2-yl)cyclopropyl)ketone (2.24 g, 4.8 mmol) was dissolved in tetrahydrofuran (30 mL), and hydrochloric acid (6 M, 8 mL, 48 mmol) was added, after the addition, the mixture was warmed to 50° C. and stirred for 3 hours. The reaction mixture was cooled to rt and diluted with water (20 mL), and adjusted with potassium carbonate solid to alkalinity, the resulting mixture was extracted with ethyl acetate (30 mL×2). The organic layers were combined and washed with saturated brine WO 2019/149158 PCT/CN2019/073303 (10 mL), dried over anhydrous sodium sulfate, filtered, and concentrated under vacuum. The residue was purified by silica gel column chromatography (PE/EtOAc (v/v)=20/1) to give the title compound as a yellow oil (1.56 g, 77%).

Step 3: 5-bromo-2-(1-(3-bromo-6-methoxypyridin-2-yl)cyclopropylcarbonyl)phenylmethylcarbonate Under nitrogen, (4-bromo-2-hydroxyphenyl)(1-(3-bromo-6-methoxypyridin-2-yl)cyclopropyl)ketone (1.56 g, 3.7 mmol) was dissolved in dry tetrahydrofuran (40 mL), and triethylamine (0.77 mL, 5.5 mmol) and methylclhlorofonmate (0.33 mL, 4.2 mmol) were added dropwise in an ice bath, after the addition, the mixture was stirred in the ice bath for 1.5 hours. The mixture was filtered to get the title compound in tetrahydrofuran as a light yellow solution (1.7 g, 96%), which was used in the next step without further purification.

Step 4: 5-bromo-2-((1-(3-bromo-6-methoxypyridin-2-yl)cyclopropyl)methyl)phenol

Sodium borohydride (0.552 g, 14.6 mmol) was dissolved in water (20 mL), a solution of 5-bromo-2-(1-(3-bromo-6-methoxypyridin-2-yl)cyclopropylcarbonyl)phenylmethylcarbonate (1.7 g, 3.7 mmol) in tetrahydrofuran was added dropwise in an ice bath (40 mL), after the addition, the mixture was stirred at rt overnight. The mixture was diluted with water (100 mL) and extracted with ethyl acetate (100 mL×2). The organic layers were combined and washed with saturated brine (20 mL), dried over anhydrous sodium sulfate, filtered, and concentrated under vacuum. The residue was purified by silica gel column chromatography (PE/EtOAc (v/v)=20/1) to give the title compound as a yellow oil (1.3 g, 86%).

MS (ESI, pos. ion) m/z: 411.9 [M+H]$^+$.

Step 5: 7-bromo-2-methoxy-10H-spiro[benzo[6,7]oxepino[3,2-b]pyridine-11,1'-cyclopropane]

Under nitrogen, cuprous iodide (28 mg, 0.15 mmol), N,N-dimethylglycine (30 mg, 0.30 mmol), cesium carbonate (470 mg, 1.4 mmol) and 5-bromo-2-((1-(3-bromo-6-methoxypyridin-2-yl)cyclopropyl)methyl)phenol (300 mg, 0.70 mmol) were dissolved in 1,4-dioxane (20 mL), the mixture was warmed to reflux and stirred for 2.5 hours. The reaction mixture was cooled to room temperature and filtered, the filtrate was concentrated under vacuum. The residue was purified by silica gel column chromatography (PE/EtOAc (v/v)=20/1) to give the title compound as a colorless oil (92 mg, 40%).

MS (ESI, pos. ion) m/z: 332.0 [M+H]$^+$.

Step 6: methyl 2-methoxy-10H-spiro[benzo[6,7]oxepino[3,2-b]pyridine-11,1'-cyclopropane]-7-carboxylate 7-Bromo-2-methoxy-10H-spiro[benzo[6,7]oxepino[3,2-b]pyridine-11,1'-cyclopropane](0.44 g, 1.3 mmol), triethylamine (0.4 mL, 3.0 mmol) and 1,1'-bis(diphenylphosphino)ferrocene]dichloropalladium(II) (10 mg, 0.015 mmol) were dissolved in methanol (30 mL), the solution was stirred in an autoclave under carbon monoxide (3.0 MPa) at 100° C. for 2 days. The mixture was cooled to rt, and concentrated under vacuum, the residue was purified by silica gel column chromatography (PE/EtOAc (v/v)=30/1) to give the title compound as a white solid (280 mg, 68%).

$^1$H NMR (400 MHz, CDCl$_3$) δ 7.86-7.80 (m, 2H), 7.41 (d, J=8.6 Hz, 1H), 7.25 (d, J=7.7 Hz, 1H), 6.45 (d, J=8.6 Hz, 1H), 3.92 (s, 3H), 3.78 (s, 3H), 3.10 (s, 2H), 1.43-1.40 (m, 2H), 0.86-0.82 (m, 2H).

Step 7: methyl 2-hydroxy-10H-spiro[benzo[6,7]oxepino[3,2-b]pyridine-11,1'-cyclopropane]-7-carboxylate Methyl 2-methoxy-10H-spiro[benzo[6,7]oxepino[3,2-b]pyridine-11,1'-cyclopropane]-7-carboxylate (280 mg, 0.9 mmol) and sodium iodide (270 mg, 1.8 mmol) were dissolved in acetonitrile (9 mL), and chlorotrimethylsilane (0.15 mL, 1.7 mmol) was added at rt, after the addition, the mixture was warmed to 85° C. and stirred for 3 hours. The mixture was cooled to rt and quenched with saturated aqueous sodium thiosulfate (50 mL). The resulting mixture was extracted with ethyl acetate (50 mL×2). The organic layers were combined and washed with saturated brine (30 mL), dried over anhydrous sodium sulfate, filtered, and concentrated under vacuum. The residue was purified by silica-gel column chromatography (DCM/MeOH=15/1, V/V) to give the title compound as a yellow solid (230 mg, 82%).

Step 8: methyl 2-((5-cyclopropyl-3-(2-(trifluoromethoxy)phenyl)isoxazol-4-yl)methoxy)-10H-spiro[benzo[6,7]oxepino[3,2-b]pyridine-11,1'-cyclopropane]-7-carboxylate 4-(Chloromethyl)-5-cyclopropyl-3-(2-(trifluromethoxy)phenyl)isoxazole (400 mg, 1.26 mmol), methyl 2-hydroxy-10H-spiro[benzo[6,7]oxepino[3,2-b]pyridine-11,1'-cyclopropane]-7-carboxylate (486 mg, 1.64 mmol) and potassium phosphate (800 mg, 3.76 mmol) were dissolved in N,N-dimethylformamide (10 mL), the mixture was warmed to 60° C. and stirred for 7 hours. The reaction mixture was cooled to rt and diluted with water (100 mL), the resulting mixture was extracted with ethyl acetate (100 mL×2). The organic layers were combined and washed with saturated brine (20 mL), dried over anhydrous sodium sulfate, filtered, and concentrated under vacuum. The residue was purified by silica gel column chromatography (PE/EtOAc (v/v)=30/1) to give the title compound as a colorless oil (616 mg, 85%).

MS (ESI, pos. ion) m/z: 580.9 [M+H]$^+$.

Step 9: 2-((5-cyclopropyl-3-(2-(trifluoromethoxy)phenyl)isoxazol-4-yl)methoxy)-10H-Spiro[benzo[6,7]oxepino[3,2-b]pyridine-11,1'-cyclopropane]-7-carboxylic acid Methyl 2-((5-cyclopropyl-3-(2-(trifluoromethoxy)phenyl)isoxazol-4-yl)methoxy)-10H-spiro[benzo[6,7]oxepino[3,2-b]pyridine-11,1'-cyclopropane]-7-carboxylate (616 mg, 1.0 mmol) was dissolved in a mixed solvent of tetrahydrofuran (10 mL) and methanol (10 mL), to the mixture was added a solution of sodium hydroxide (225 mg, 6.4 mmol) in water (10 mL), the resulting mixture was stirred at rt overnight. The reaction mixture was concentrated under vacuum to remove the most solvent. The mixture was diluted with water (10 mL) and acidified with hydrochloric acid (2 M, 5 mL), and the resulting mixture was extracted with EtOAc (100 mL×2). The organic layers were combined and washed with saturated brine (10 mL), dried over anhydrous sodium sulfate, filtered, and concentrated under vacuum to give a crude product, the crude product was purified by silica gel column chromatography (dichloromethane/methanol (v/v)=100/1) to give the title compound as a white solid (600 mg, 99%).

MS (ESI, pos. ion) m/z: 565.2 [M+H]$^+$;
$^1$H NMR (400 MHz, CDCl$_3$) δ 7.99-7.79 (m, 2H), 7.60-7.43 (m, 2H), 7.43-7.22 (m, 4H), 6.31 (d, J=8.6 Hz, 1H), 5.05 (s, 2H), 3.09 (s, 2H), 2.23-2.09 (m, 1H), 1.32-1.19 (m, 6H), 1.16-1.05 (m, 2H).

Example 4: 2-((5-cyclopropyl-3-(2-(trifluoromethoxy)phenyl)isoxazol-4-yl)methoxy)-11,11-dimethyl-10,11-dihydrobenzo[6,7]oxepino[3,2-b]pyridine-7-carboxylic acid

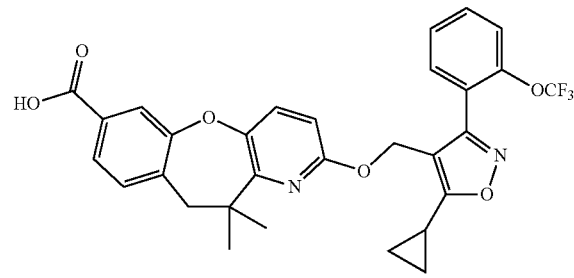 [SMILES: CC1(C)Cc2ccc(C(=O)O)cc2Oc2ccc(OCc3c(-c4ccccc4OC(F)(F)F)noc3C3CC3)nc21]

Step 1: methyl 2-((5-cyclopropyl-3-(2-(trifluromethoxy)phenyl)isoxazol-4-yl)methoxy)-11,11-dimethyl-10,11-dihydrobenzo[6,7]oxepino[3,2-b]pyridine-7-carboxylate 4-(Chloromethyl)-5-cyclopropyl-3-(2-(trifluoromethoxy)phenyl)isoxazole (290 mg, 0.95 mmol), methyl 2-hydroxy-11,11-dimethyl-10,11-dihydrobenzo[6,7]oxepino[3,2-b]pyridine-7-carboxylate (300 mg, 1.0 mmol) and potassium phosphate (638 mg, 3.0 mmol) were dissolved in N,N-dimethylformamide (15 mL), the mixture was warmed to 60° C. and stirred for 6 hours. The reaction mixture was cooled to rt and diluted with water (150 mL), the resulting mixture was extracted with ethyl acetate (100 mL×2). The organic layers were combined and washed with saturated brine (20 mL), dried over anhydrous sodium sulfate, filtered, and concentrated under vacuum. The residue was purified by silica gel column chromatography (PE/EtOAc (v/v)=50/1) to give the title compound as a colorless oil (580 mg, 100%).

MS (ESI, pos. ion) m/z: 580.9 [M+H]$^+$.

Step 2: 2-((5-cyclopropyl-3-(2-(trifluoromethoxy)phenyl)isoxazol-4-yl)methoxy)-11,11-dimethyl-10,11-dihydrobenzo[6,7]oxepino[3,2-b]pyridine-7-carboxylic acid Methyl 2-((5-cyclopropyl-3-(2-(trifluoromethoxy)phenyl)isoxazol-4-yl)methoxy)-11,11-dimethyl-10,11-dihydrobenzo[6,7]oxepino[3,2-b]pyridine-7-carboxylate (580 mg, 1.0 mmol) was dissolved in a mixed solvent of tetrahydrofuran (15 mL) and methanol (15 mL), to the mixture was added a solution of sodium hydroxide (119 mg, 3.0 mmol) in water (10 mL), the resulting mixture was stirred at rt overnight. The reaction mixture was concentrated under vacuum to remove the most solvent. The mixture was diluted with water (10 mL) and acidified with hydrochloric acid (2 M, 5 mL), and the resulting mixture was extracted with EtOAc (100 mL×2). The organic layers were combined and washed with saturated brine (10 mL), dried over anhydrous sodium sulfate, filtered, and concentrated under vacuum to give a crude product, the crude product was purified by silica gel column chromatography (dichloromethane/methanol (v/v)=50/1) to give the title compound as a white solid (460 mg, 81%).

MS (ESI, pos. ion) m/z: 566.8 [M+H]$^+$;
$^1$H NMR (400 MHz, CDCl$_3$) δ 7.87 (dd, J=10.0, 2.2 Hz, 2H), 7.55 (dd, J=7.8, 1.6 Hz, 1H), 7.51-7.45 (m, 1H), 7.39 (d, J=8.6 Hz, 1H), 7.37-7.31 (m, 3H), 6.38 (d, J=8.6 Hz, 1H), 5.18 (s, 2H), 3.15 (s, 2H), 2.23-2.11 (m, 1H), 1.29 (s, 6H), 1.26-1.22 (m, 2H), 1.13-1.07 (m, 2H).

Example 5: 2-((5-cyclopropyl-3-(2,4-dichlorophenyl)isoxazol-4-yl)methoxy)-10H-spiro[benzo[6,7]oxepino[3,2-b]pyridine-11,1'-cyclopropane]-7-carboxylic acid

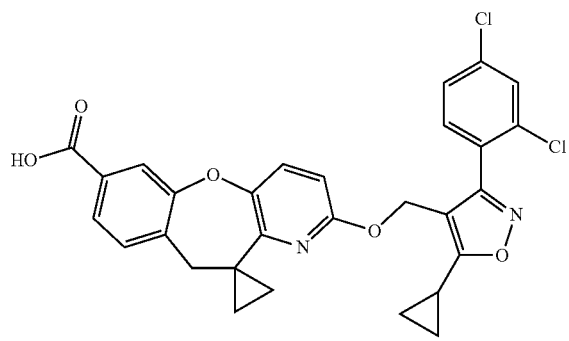 [SMILES: O=C(O)c1ccc2c(c1)Oc1ccc(OCc3c(-c4ccc(Cl)cc4Cl)noc3C3CC3)nc1C1(CC1)C2]

Step 1: 2,4-dichlorobenzaldoxime 2,4-Dichlorobenzaldehyde (10.0 g, 57.1 mmol) was dissolved in ethanol (80 mL), and hydroxylamine hydrochloride (4.8 g, 70 mmol) and a solution of sodium carbonate (3.33 g, 31.4 mmol) in water (30 mL) were added, the mixture was stirred at 60° C. for 4 hours. The mixture cooled to rt and concentrated under vacuum to remove ethanol, the residue was diluted with water (600 mL), and stirred for 1 hour, the mixture was filtered by suction, the filter cake was dried to give the title compound as a white solid (10.5 g, 96.3%).

MS (ESI, pos. ion) m/z: 190.0 [M+H]$^+$.

Step 2: 2,4-dichloro-N-hydroxy-chlorobenzaldoxime

A solution of N-chlorosuccinimide (8.8 g, 66.0 mmol) in N,N-dimethylformamide (100 mL) was added into a solution of 2,4-dichlorobenzaldoxime (10.5 g, 55.0 mmol) in N,N-dimethylformamide (100 mL), the mixture was stirred at rt overnight. The mixture was diluted with water (0.3 L) and extracted with ethyl acetate (150 mL), the organic layer was concentrated under vacuum to give the title compound as a light yellow oil (12.4 g, 100%).

Step 3: methyl 5-cyclopropyl-3-(2,4-dichlorophenyl)isoxazole-4-carboxylate 2,4-Dichloro-N-hydroxy-chlorobenzaldoxime (12.4 g, 55.0 mmol) was dissolved in triethylamine (100 mL), to the mixture methyl 3-cyclopropyl-3-oxopropionate (11.7 g, 82.6 mmol) was added at rt, and then the mixture was stirred for 17 hours. The reaction mixture was concentrated under vacuum, the residue was diluted with water (300 mL), and the resulting mixture was extracted with EtOAc (150 mL×2). The combined organic phases were dried over anhydrous sodium sulfate, concentrated in vacuo. The residue was purified by silica gel chromatograph (PE/EtOAc (v/v)=50/1) to give the title compound as a yellow solid (17.0 g, 99%).

MS (ESI, pos. ion) m/z: 314.2 [M+H]$^+$.

Step 4: (5-cyclopropyl-3-(2,4-dichlorophenyl)isoxazol-4-yl)methanol

Under nitrogen, a mixture of lithium aluminum hydride (2.27 g, 59.8 mmol) in tetrahydrofuran (60 mL) was added into a solution of methyl 5-cyclopropyl-3-(2,4-dichlorophenyl)isoxazole-4-carboxylate (17.0 g, 54.4 mmol) in tetrahydrofuran (60 mL) slowly in an ice bath, after the addition, the mixture was warmed to rt and stirred at rt for 9 hours. The reaction mixture was quenched with saturated aqueous ammonium chloride and diluted with water (150 mL), then concentrated hydrochloric acid (5 mL) was added, and the resulting mixture was extracted with EtOAc (80 mL×2). The combined organic layers were dried over anhydrous sodium sulfate, and filtered. The filtrate was concentrated in vacuo. The residue was purified by silica gel column chromatography (PE/EtOAc (v/v)=30/1) to give the title compound as a colorless oil (3.32 g, 21.5%).

MS (ESI, pos. ion) m/z: 284.0 [M+H]$^+$.

Step 5: 4-(chloromethyl)-5-cyclopropyl-3-(2,4-dichlorophenyl)isoxazole

Benzotriazole (2.1 g, 18 mmol) was dissolved in dichloromethane (20 mL), to the solution was added thionyl chloride (1.28 mL, 17.6 mmol) dropwise under nitrogen in an ice bath, after the addition, the mixture was warmed to rt and stirred for 1.5 hours. The above reaction mixture was added into a solution of (5-cyclopropyl-3-(2,4-dichlorophenyl)isoxazol-4-yl)methanol (3.34 g, 11.8 mmol) in dichloromethane (20 mL) dropwise under nitrogen, the resulting mixture was stirred overnight. The reaction mixture was diluted with water (100 mL), and extracted with dichloromethane (100 mL×2). The combined organic layers were dried over anhydrous sodium sulfate, and filtered. The filtrate was concentrated in vacuo. The residue was purified by silica gel column chromatography (PE/EtOAc (v/v)=50/1) to give the title compound as a colorless oil (1.5 g, 42%).

Step 6: methyl 2-((5-cyclopropyl-3-(2,4-dichlorophenyl)isoxazol-4-yl)methoxy)-10H-Spiro[benzo[6,7]oxepino[3,2-b]pyridine-11,1'-cyclopropane]-7-carboxylate 4-(Chloromethyl)-5-cyclopropyl-3-(2,4-dichlorophenyl)isoxazole (400 mg, 1.3 mmol), methyl 2-hydroxy-10H-spiro[benzo[6,7]oxepino[3,2-b]pyridine-11,1'-cyclopropane]-7-carboxylate (393 mg, 1.3 mmol) and potassium phosphate (0.84 g, 3.9 mmol) were dissolved in N,N-dimethylformamide (15 mL), the mixture was warmed to 60° C. and stirred for 7 hours. The reaction mixture was cooled to rt and diluted with water (100 mL), the resulting mixture was extracted with ethyl acetate (50 mL×2). The organic layers were combined and washed with saturated brine (100 mL), dried over anhydrous sodium sulfate, filtered, and concentrated under vacuum. The residue was purified by silica gel column chromatography (PE/EtOAc (v/v)=50/1) to give the title compound as a colorless oil (600 mg, 81%).

Step 7: 2-((5-cyclopropyl-3-(2,4-dichlorophenyl)isoxazol-4-yl)methoxy)-10H-spiro[benzo[6,7]oxepino[3,2-b]pyridine-11,1'-cyclopropane]-7-carboxylic acid Methyl 2-((5-cyclopropyl-3-(2,4-dichlorophenyl)isoxazol-4-yl)methoxy)-10H-spiro[benzo[6,7]oxepino[3,2-b]pyridine-11,1'-cyclopropane]-7-carboxylate (600 mg, 1.1 mmol) was dissolved in a mixed solvent of tetrahydrofuran (5 mL) and methanol (5 mL), to the mixture was added a solution of sodium hydroxide (127 mg, 3.2 mmol) in water (5 mL), the resulting mixture was stirred at rt overnight. The reaction mixture was concentrated under vacuum to remove the most solvent. The mixture was diluted with water (100 mL) and acidified with hydrochloric acid (2 M, 5 mL), and the resulting mixture was extracted with EtOAc (50 mL×2). The organic layers were combined and washed with saturated brine (10 mL), dried over anhydrous sodium sulfate, filtered, and concentrated under vacuum to give a crude product, the crude product was purified by silica gel column chromatography (dichloromethane/methanol (v/v)=100/1) to give the title compound as a white solid (500 mg, 85.5%).

MS (ESI, pos. ion) m/z: 549.0 [M+H]$^+$;

$^1$H NMR (400 MHz, CDCl$_3$) δ 7.88 (dd, J=3.9, 2.4 Hz, 2H), 7.48 (d, J=1.8 Hz, 1H), 7.39 (d, J=8.6 Hz, 1H), 7.35-7.23 (m, 3H), 6.32 (d, J=8.6 Hz, 1H), 5.04 (s, 2H), 3.10 (s, 2H), 2.14-2.08 (m, 1H), 1.28-1.21 (m, 4H), 1.17-1.06 (m, 2H), 0.88-0.77 (m, 2H).

Example 6: 2-((5-cyclopropyl-3-(2,6-dichloro-4-fluorophenyl)isoxazol-4-yl)methoxy)-10H-Spiro[benzo[6,7]oxepino[3,2-b]pyridine-11,1'-cyclopropane]-7-carboxylic acid

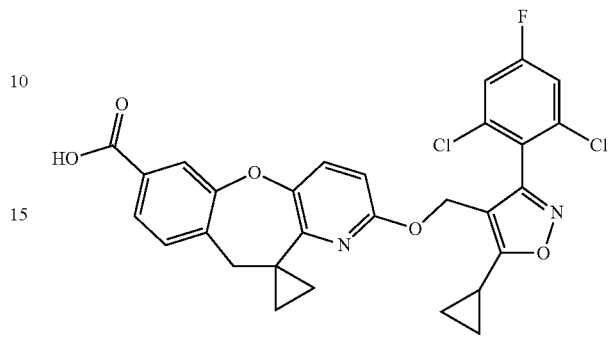

Step 1: 2,6-dichloro-4-fluorobenzaldoxime 2,6-Dichloro-4-fluorobenzaldehyde (10.0 g, 52.8 mmol) was dissolved in ethanol (80 mL), and hydroxylamine hydrochloride (4.4 g, 63 mmol) and a solution of sodium carbonate (3.1 g, 29 mmol) in water (18 mL) were added, the mixture was stirred at 60° C. for 4 hours. The mixture was cooled to rt and concentrated under vacuum to remove ethanol, the residue was diluted with water (300 mL), and stirred for 1 hour, the mixture was filtered by suction, the filter cake was dried to give the title compound as a white solid (10.7 g, 99.3%).

Step 2: 2,6-dichloro-4-fluoro-N-hydroxy-chlorobenzaldoxime

A solution of N-chlorosuccinimide (8.3 g, 62.5 mmol) in N,N-dimethylformamide (100 mL) was added into a solution of 2,6-dichloro-4-fluorobenzaldoxime (10.8 g, 52.0 mmol) in N,N-dimethylformamide (100 mL), the mixture was stirred at rt overnight. The mixture was diluted with water (0.5 L) and extracted with ethyl acetate (150 mL), the organic layer was concentrated under vacuum to give the title compound as a colorless oil (12.6 g, 100%).

Step 3: methyl 5-cyclopropyl-3-(2,6-dichloro-4-fluorophenyl)isoxazole-4-carboxylate 2,6-Dichloro-4-fluoro-N-hydroxy-chlorobenzaldoxime (12.6 g, 52.0 mmol) was dissolved in triethylamine (100 mL), to the mixture methyl 3-cyclopropyl-3-oxopropionate (11.1 g, 78.1 mmol) was added at rt, and then the mixture was stirred for 17 hours. The reaction mixture was concentrated under vacuum, the residue was diluted with water (500 mL), and the resulting mixture was extracted with EtOAc (150 mL×2). The combined organic phases were dried over anhydrous sodium sulfate, concentrated in vacuo. The residue was purified by silica gel chromatograph (PE/EtOAc (v/v)=100/1) to give the title compound as a yellow solid (11.0 g, 64%).

MS (ESI, pos. ion) m/z: 331.0 [M+H]$^+$.

Step 4: (5-cyclopropyl-3-(2,6-dichloro-4-fluorophenyl)isoxazol-4-yl)methanol

Under nitrogen, a mixture of lithium aluminum hydride (1.15 g, 30.3 mmol) in tetrahydrofuran (60 mL) was added into a solution of methyl 5-cyclopropyl-3-(2,6-dichlorophenyl)isoxazole-4-carboxylate (5.0 g, 15.2 mmol) in tetrahydrofuran (60 mL) slowly in an ice bath, after the addition, the mixture was warmed to rt and stirred at rt overnight. The reaction mixture was quenched with saturated aqueous ammonium chloride and diluted with water (150 mL), then concentrated hydrochloric acid (3 mL) was added, and the resulting mixture was extracted with EtOAc (150 mL×2). The combined organic layers were dried over anhydrous sodium sulfate, and filtered. The filtrate was concentrated in vacuo. The residue was purified by silica gel column chromatography (PE/EtOAc (v/v)=30/1) to give the title compound as a white solid (4.1 g, 90%).

Step 5: 4-(chloromethyl)-5-cyclopropyl-3-(2,6-dichloro-4-fluorophenyl)isoxazole

Benzotriazole (2.4 g, 20.4 mmol) was dissolved in dichloromethane (15 mL), to the solution was added thionyl chloride (1.48 mL, 20.4 mmol) dropwise under nitrogen in an ice bath, after the addition, the mixture was warmed to rt and stirred for 1.5 hours. The above reaction mixture was added into a solution of (5-cyclopropyl-3-(2,6-dichloro-4-fluorophenyl)isoxazol-4-yl)methanol (4.1 g, 13.6 mmol) in dichloromethane (15 mL) dropwise under nitrogen, the resulting mixture was stirred for 16 hours. The reaction mixture was diluted with water (200 mL), and extracted with dichloromethane (100 mL×2). The combined organic layers were dried over anhydrous sodium sulfate, and filtered. The filtrate was concentrated in vacuo. The residue was purified by silica gel column chromatography (PE/EtOAc (v/v)=100/1) to give the title compound as a light yellow oil (2.6 g, 60%).

MS (ESI, pos. ion) m/z: 321.8 [M+H]+.

Step 6: methyl 2-((5-cyclopropyl-3-(2,6-dichloro-4-fluorophenyl)isoxazol-4-yl)methoxy)-10H-spiro[benzo[6,7]oxepino[3,2-b]pyridine-11,1'-cyclopropane]-7-carboxylate 4-(Chloromethyl)-5-cyclopropyl-3-(2,6-dichloro-4-fluorophenyl)isoxazole (968 mg, 3.0 mmol), methyl 2-hydroxy-10H-spiro[benzo[6,7]oxepino[3,2-b]pyridine-11,1'-cyclopropane]-7-carboxylate (1.35 g, 4.5 mmol) and potassium phosphate (1.93 g, 9.1 mmol) were dissolved in N,N-dimethylformamide (15 mL), the mixture was warmed to 60° C. and stirred overnight. The reaction mixture was cooled to rt and diluted with water (150 mL), the resulting mixture was extracted with ethyl acetate (100 mL×2). The organic layers were combined and washed with saturated brine (100 mL), dried over anhydrous sodium sulfate, filtered, and concentrated under vacuum. The residue was purified by silica gel column chromatography (PE/EtOAc (v/v)=50/1) to give the title compound as a colorless oil (631 mg, 36%).

MS (ESI, pos. ion) m/z: 581.0 [M+H]±.

Step 7: 2-((5-cyclopropyl-3-(2,6-dichloro-4-fluorophenyl)isoxazol-4-yl)methoxy)-10H-Spiro[benzo[6,7]oxepino[3,2-b]pyridine-11,1'-cyclopropane]-7-carboxylic acid Methyl 2-((5-cyclopropyl-3-(2,6-di chloro-4-fluorophenyl)isoxazol-4-yl)methoxy)-10H-spiro[benzo[6,7]oxepino[3,2-b]pyridine-11,1'-cyclopropane]-7-carboxylate (631 mg, 1.1 mmol) was dissolved in a mixed solvent of tetrahydrofuran (15 mL) and methanol (15 mL), to the mixture was added a solution of sodium hydroxide (130 mg, 3.3 mmol) in water (10 mL), and the resulting mixture was stirred at rt overnight. The reaction mixture was concentrated under vacuum to remove the most solvent. The mixture was diluted with water (100 mL) and acidified with hydrochloric acid (2 M, 5 mL), and the resulting mixture was extracted with EtOAc (50 mL×2). The organic layers were combined and washed with saturated brine (10 mL), dried over anhydrous sodium sulfate, filtered, and concentrated under vacuum to give a crude product, the crude product was purified by silica gel column chromatography (dichloromethane/methanol (v/v)=100/1) to give the title compound as a white solid (400 mg, 65%).

$^1$H NMR (400 MHz, CDCl$_3$) δ 7.93-7.81 (m, 2H), 7.37 (d, J=8.6 Hz, 1H), 7.26 (s, 1H), 7.11 (d, J=8.1 Hz, 2H), 6.30 (d, J=8.6 Hz, 1H), 5.00 (s, 2H), 3.09 (s, 2H), 2.16-2.09 (m, 1H), 1.28-1.23 (m, 4H), 1.16-1.09 (m, 2H), 0.86-0.79 (m, 2H).

Example 7: 2-((5-cyclopropyl-3-(2,6-dichloro-4-fluorophenyl)isoxazol-4-yl)methoxy)-10,11-dihydrobenzo[6,7]oxepino[3,2-b]pyridine-7-carboxylic acid

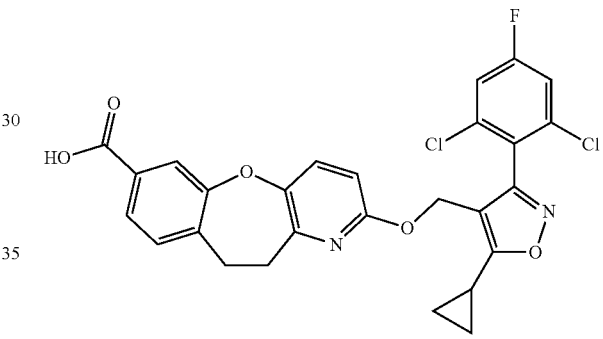

Step 1: methyl 2-((5-cyclopropyl-3-(2,6-dichloro-4-fluorophenyl)isoxazol-4-yl)methoxy)-10,11-dihydrobenzo[6,7]oxepino[3,2-b]pyridine-7-carboxylate 4-(Chloromethyl)-5-cyclopropyl-3-(2,6-dichloro-4-fluorophenyl)isoxazole (1.77 g, 5.5 mmol), methyl 2-hydroxy-10,11-dihydrobenzo[6,7]oxepino[3,2-b]pyridine-7-carboxylate (2.25 g, 8.3 mmol) and potassium phosphate (3.52 g, 16.6 mmol) were dissolved in N,N-dimethylformamide (15 mL), the mixture was warmed to 60° C. and stirred for 6 hours. The reaction mixture was cooled to rt and diluted with water (200 mL), the resulting mixture was extracted with ethyl acetate (100 mL×2). The organic layers were combined and washed with saturated brine (20 mL), dried over anhydrous sodium sulfate, filtered, and concentrated under vacuum. The residue was purified by silica gel column chromatography (PE/EtOAc (v/v)=50/1) to give the title compound as a colorless oil (2.55 g, 83%).

MS (ESI, pos. ion) m/z: 555.1 [M+H]+.

Step 2: 2-((5-cyclopropyl-3-(2,6-dichloro-4-fluorophenyl)isoxazol-4-yl)methoxy)-10,11-dihydrobenzo[6,7]oxepino[3,2-b]pyridine-7-carboxylic acid Methyl 2-((5-cyclopropyl-3-(2,6-dichloro-4-fluorophenyl)isoxazol-4-yl)methoxy)-10,11-dihydrobenzo[6,7]oxepino[3,2-b]pyridine-7-carboxylate (2.55 g, 4.6 mmol) was dissolved in a mixed solvent of tetrahydrofuran (30 mL) and methanol (30 mL), to the mixture was added a solution of sodium hydroxide (550 mg, 13.7 mmol) in water (20 mL), then the resulting mixture was stirred at rt overnight. The reaction mixture was concentrated under vacuum to remove the most solvent. The mixture was diluted with water (10 mL) and acidified with hydrochloric acid (2 M, 15 mL), and the resulting mixture was extracted with EtOAc (100 mL×2). The organic layers were combined and washed with saturated brine (10 mL), dried over anhydrous sodium sulfate, filtered, and concentrated under vacuum to give a crude product, the crude product was purified by silica gel column chromatography (dichloromethane/methanol (v/v)= 100/1) to give the title compound as a white solid (1.73 g, 70%).

MS (ESI, pos. ion) m/z: 541.0 $[M+H]^+$;

$^1$H NMR (400 MHz, CDCl$_3$) δ 7.87 (s, 1H), 7.84 (d, J=8.0 Hz, 1H), 7.40 (d, J=8.7 Hz, 1H), 7.31 (d, J=7.8 Hz, 1H), 7.14 (d, J=8.0 Hz, 2H), 6.43 (d, J=8.7 Hz, 1H), 5.12 (s, 2H), 3.31-3.17 (m, 2H), 3.16-3.01 (m, 2H), 2.41-2.25 (m, 1H), 1.34-1.23 (m, 2H), 1.20-1.06 (m, 2H).

Example 8: Coactivation of TR-FRET Farnesoid X Receptor Protein

1. Test Method
Purchasing Invitrogen PV4833 Kit.

Step 1, the compound was weighed and dissolved in 100% DMSO, the highest concentration is 3000 μM, and then diluted with DMSO by 3-fold serial dilution to get 10 concentrations.

Step 2, the above formulated compound solutions were diluted 100 times with the buffer provided in the kit, which were mixed respectively and 10 μL of which were added into a 384 well plate in turn.

Step 3, FXR recombinant nucleo receptor protein was diluted with a buffer to formulate 4× concentration, and 5 μL of which was added into the above 384 well plate containing the compound.

Step 4, Fluorescein-SRC2-2 and Tb anti-GST antibody were diluted with a buffer respectively, both concentration are 4×, after the two reagents were mixed together, 10 μL of which was added into the 384 well plate described in step 3.

At last, the solution in the 384 well plate was blend by centrifugation, and then incubated at room temperature for 1 hour. And then the detection was performed at 520, 495 and 337 nm wavelengths by TR-FRET endpoint method, EC$_{50}$ values were calculated using the detection values of ER=520 nm/495 nm wavelength.

2. Results

TABLE 2

Results of coactivation of TR-FRET farnesoid X receptor protein

| No. | EC$_{50}$ (nM) |
|---|---|
| Obeticholic Acid | 75 |
| Example 1 | 3.4 |
| Example 3 | 8.6 |
| Example 6 | 2 |
| Example 7 | 7.4 |

3. Conclusion

It can be known from the EC$_{50}$ values listed in table 2, the compounds of the invention show better activity, which have good activation for farnesoid X receptor protein.

Example 9: Assay of Singlehybrid Dual-Luciferase Reporter Gene in Mammal

Single hybridization of mammal cell is also known as GAL4 chimeric receptor gene detection method, which is a new technique for screening and evaluating the function of nuclear receptor and the physiological activity of its ligand. At the same time, FXR activity is detected by dual-luciferase reporter gene as described below. The vector PBIND-FXR (promega, Promega Biotechnology Co., Ltd.) contains cDNA of FXR ligand binding domain, GeneBank NO. is Q96RI1.2, amino acid sequence is 261-481, and also contains DBD binding domain of GAL4 and Ranilla luciferase gene, The vector pG5Luc (promega, Promega Biotechnology Co., Ltd.) contains firefly luciferase reporter gene. All assay of GAL4 reporter gene are performed in HEK293 cell.

The cell was incubated in a cell incubator at 37° C., 5% CO2. Cell plating and transfection: The transfection reagent is FuGENE HD transfection solution. The steps are as follows: two plasmids pBIND-FXR and pG5Luc, transfection solution FuGENE HD, serum-free medium, total suspension 2.5 ml/well were prepared for transfection. The above suspension was shook vigorously, and placed at rt for 15 min. Cells were placed into 96 well plate at a density of 600 000 per well.

Calculation of the results: Activation %=[(X−Min)/ (Max−Min)]×100%; wherein X represents ratio of firefly fluorescence to Ranilla luciferase in the compound well, Min represents ratio without compound, Max represents ratio of the highest concentration of the positive drug.

TABLE 3 results of GAL4 reporter gene assay

| No. | EC$_{50}$ (nM) |
|---|---|
| Obeticholic Acid | 250 |
| Example 1 | 1.64 |

It can be known from the EC$_{50}$ values listed in table 3, the compounds of the invention show better activity, which can activate farnesoid X receptor protein to regulate expression of downstream related genes.

Example 10: Liver Microsome Stability Test

The solution of compound in DMSO (10 mM) was diluted with a mixed solvent of acetonitrile and water (1:1, v/v) to get a 100 μM compound solution, and then the 100 μM compound solution was diluted with potassium phosphate buffer (0.1 M, pH 7.4) to get a 3 μM compound solution. NADPH was formulated with potassium phosphate buffer (0.1 M, pH 7.4) to NADPH solution (6 mM). Rat liver microsome was formulated with potassium phosphate buffer (0.1 M, pH 7.4) to liver microsome solution (1.5 mg/mL).

The total volume of incubation mixture was 45 μL, including 15 μL rat liver microsome solution (1.5 mg/mL), 15 μL compound solution (3 μM) and 15 μL NADPH solution (6 mM), the final concentration of liver microsome in the incubation mixture was 0.5 mg/mL, the compound concentration was 1 μM, the NADPH concentration was 2 mM.

The incubation mixture was incubated at 37° C. The reaction was terminated by adding 120 μL acetonitrile solution containing internal standard at different time points (20 min and 60 min), and centrifuged at 4000 rpm for 5 min. The supernatant was took out and analyzed by LC-MS/MS.

At the same time, a parallel incubation test was set up, using inactivated rat liver microsomes as negative control and verapamil at the same concentration as positive control. The reaction was incubated at 37° C. and terminated at different time points (20 minutes and 60 minutes).

The ratio of sample peak area to internal standard peak area was obtained by analyzing through LC/MS/MS, the drug content of the negative control was as 100%, the drug relative content at each time point was calculated. The rate constant was obtained by plotting based on "Log[compound concentration]" to "incubating time", and then the half-life $T_{1/2}$ and intrinsic clearance $CL_{Hep}$ of the compound were calculated.

TABLE 4

Stability data of the example of the present invention in rat liver microsomes

| | Rats | | |
|---|---|---|---|
| Examples | Concentration (μM) | $T_{1/2}$ (min) | $Cl_{Hep}$ (mL/min/kg) |
| Example 2 | 1 | 28.77 | 86.33 |
| Example 3 | 1 | 26.82 | 92.61 |
| Example 5 | 1 | 25.03 | 99.23 |

Example 11: Pharmacokinetic Test

1. Test Method

Experimental animals: 6 healthy male adult SD rats (purchased from Hunan SJA Laboratory Animal Co.; Ltd) were randomized into 2 groups, 3 in each group, the groups were administered by intravenous injection and gavage respectively.

Preparation of drugs: an amount of the compound was scaled, and the target concentrate of the compound was prepared by addition of 5% DMSO, 10% Kolliphor HS15 and 85% saline (0.9%).

Administration and samples collection: the animals were fasted 12 hours before administration and provided again 3 hours post-administration, SD rats were administrated by intravenous injection from hindlimb peduncular veins (1 mg/kg) and by gavage (PO, 5 mg/kg). 200-400 μL of blood was collected at different time points 0, 0.083, 0.25, 0.5, 1, 2, 4, 6, 8, 24 h from rats tail vein. Blood collection was 200-400 μL per time point. The blood collected at each time point was placed in $K_2$EDTA anticoagulant tube, and stored at a couveuse with ice bags. All the samples in 15 min were centrifuged at 4600 r/min at 4° C. for 5 min, plasma samples were obtained, the concentrates of compound in the plasma samples were determined by LC/MS/MS, the pharmacokinetic parameters were calculated based on the drug concentration-time curve.

Pharmacokinetic properties of the compounds of the present invention were tested by the example above, and Pharmacokinetic parameters are shown in Table 4.

2. Test Results

Conclusions: seen from Table 5, the plasma concentration and exposure levels of the rats were high after oral administration of the compounds of the present invention, the clear rate was low, and the bioavailability was better, the compounds of the present invention have good pharmacokinetic characteristics.

Finally, it should be noted that there are other ways to carry out the invention.

Accordingly, embodiments of the present invention is to be described as examples, but the present invention is not limited to the contents described, further modifications may be made within the scope of the present invention or the equivalents added in the claims. All publications or patents cited herein are incorporated by reference herein.

The invention claimed is:

1. A compound having Formula (I) or a stereoisomer, a geometric isomer, a tautomer, an N-oxide, or a pharmaceutically acceptable salt thereof,

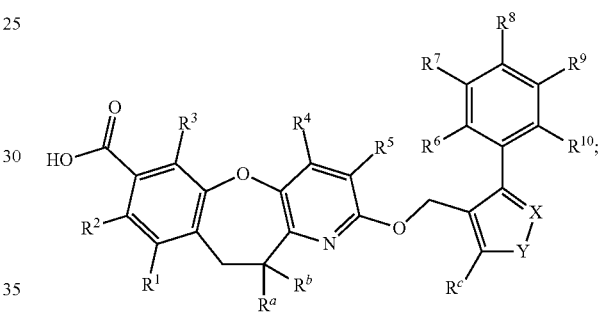

(I)

wherein

X is N or CH;

Y is O, S or NH;

each $R^a$ and $R^b$ is independently $C_{1-6}$ alkyl, $C_{1-6}$ haloalkyl, $C_{1-6}$ alkoxy, $C_{1-6}$ hydroxyalkyl or $C_{1-6}$ alkoxy-$C_{1-6}$ alkyl-; or $R^a$ and $R^b$, together with the carbon atom to which they are attached, form $C_{3-8}$ cycloalkane or 3-8 membered heterocycle which is a saturated or partially unsaturated monocyclic ring comprising one or more heteroatoms selected from O, S or N;

each $R^1$, $R^2$, $R^3$, $R^4$ and $R^5$ is independently H, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoalkyl, $C_{1-6}$ alkoxy, $C_{1-6}$ alkylamino, $C_{1-6}$ haloalkoxy or $C_{1-6}$ alkoxy-$C_{1-6}$ alkyl;

each $R^6$, $R^7$, $R^8$, $R^9$ and $R^{10}$ is independently H, deuterium, F, Cl, Br, I, hydroxy, amino, nitro, cyano, $C_{1-6}$ alkyl, $C_{1-6}$ haloalkyl, $C_{1-6}$ hydroxyalkyl, $C_{1-6}$ aminoal-

TABLE 5

Pharmacokinetic activity of the compound of the invention

| No. | administration route | dosage (mg/kg) | F(%) | $AUC_{INF}$ (h*ng/ml) | $AUC_{last}$ (h*ng/ml) | Cl (ml/min/kg) | $C_{max}$ (ng/ml) | $MRT_{INF}$ (h) | $T_{1/2}$ (h) | $T_{max}$ (h) | $V_{ss}$ (l/kg) |
|---|---|---|---|---|---|---|---|---|---|---|---|
| Example 3 | iv | 1 | 71.3 | 1740 | 1730 | 9.62 | 1660 | 1.01 | 0.774 | 0.083 | 0.584 |
| | po | 5 | | 6210 | 6170 | N/A | 2320 | 1.72 | 0.891 | 1 | N/A | kyl, $C_{1-6}$ alkoxy, $C_{1-6}$ alkylamino, $C_{1-6}$ haloalkoxy or $C_{1-6}$ alkoxy-$C_{1-6}$ alkyl or $C_{3-8}$ cycloalkyl;

$R^c$ is $C_{1-4}$ alkyl or $C_{3-6}$ cycloalkyl;

with the proviso that the compound of Formula (I) is not

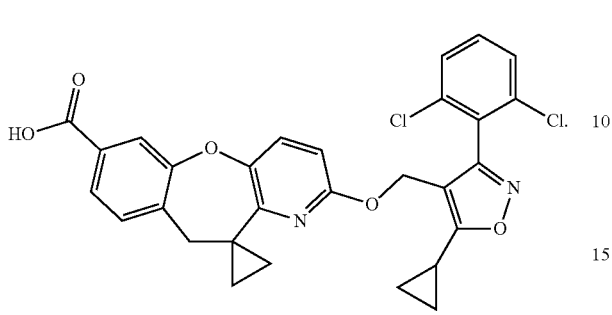

2. The compound of claim 1, wherein each $R^a$ and $R^b$ is independently $C_{1-3}$ alkyl, $C_{1-3}$ haloalkyl, $C_{1-3}$ alkoxy, $C_{1-3}$ hydroxyalkyl or $C_{1-3}$ alkoxy-$C_{1-3}$ alkyl-; or $R^a$ and $R^b$, together with the carbon atom to which they are attached, form $C_{3-6}$ cycloalkane or 3-6 membered heterocycle which is a saturated or partially unsaturated monocyclic ring comprising one or more heteroatoms selected from O, S or N.

3. The compound of claim 1, wherein each $R^a$ and $R^b$ is independently methyl, ethyl, n-propyl, isopropyl, difluoromethyl, trifluoromethyl, methoxy, ethoxy, n-propoxy, hydroxymethyl, 2-hydroxyethyl, 3-hydroxypropyl, methoxymethyl, ethoxymethyl, 2-methoxyethyl, 2-ethoxyethyl or 2-n-propoxyethyl; or $R^a$ and $R^b$, together with the carbon atom to which they are attached, form cyclopropane, cyclobutane, cyclopentane, cyclohexane, oxacyclopropane, trimethylene oxide or azetidine.

4. The compound of claim 1, wherein each $R^1$, $R^2$, $R^3$, $R^4$ and $R^5$ is independently H, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{1-3}$ haloalkoxy or $C_{1-3}$ alkoxy-$C_{1-3}$ alkyl.

5. The compound of claim 1, wherein each $R^1$, $R^2$, $R^3$, $R^4$ and $R^5$ is independently H, deuterium, F, Cl, Br, I, hydroxy, amino, nitro, cyano, methyl, ethyl, n-propyl, isopropyl, difluoromethyl, trifluoromethyl, hydroxymethyl, 1-hydroxyethyl, 2-hydroxyethyl, 3-hydroxypropyl, aminomethyl, methoxy, ethoxy, n-propoxy, methylamino, dimethylamino, trifluoromethoxy, difluoromethoxy, 2,2-difluoroethoxy, 1,2-difluoroethoxy, methoxymethyl, ethoxymethyl, 2-methoxyethyl, 2-ethoxyethyl or 2-n-propoxyethyl.

6. The compound of claim 1, wherein each $R^6$, $R^7$, $R^3$, $R^9$ and $R^{10}$ is independently H, deuterium, F, Cl, Br, I, hydroxy, amino, nitro, cyano, $C_{1-3}$ alkyl, $C_{1-3}$ haloalkyl, $C_{1-3}$ hydroxyalkyl, $C_{1-3}$ aminoalkyl, $C_{1-3}$ alkoxy, $C_{1-3}$ alkylamino, $C_{1-3}$ haloalkoxy, $C_{1-3}$ alkoxy-$C_{1-3}$ alkyl or $C_{3-6}$ cycloalkyl.

7. The compound of claim 1, wherein each $R^6$, $R^7$, $R^8$, $R^4$ and $R^{10}$ is independently H, deuterium, F, Cl, Br, I, hydroxy, amino, nitro, cyano, methyl, ethyl, n-propyl, isopropyl, difluoromethyl, trifluoromethyl, hydroxymethyl, 1-hydroxyethyl, 2-hydroxyethyl, 3-hydroxypropyl, aminomethyl, methoxy, ethoxy, n-propoxy, methylamino, dimethylamino, trifluoromethoxy, difluoromethoxy, 2,2-difluoroethoxy, 1,2-difluoroethoxy, methoxymethyl, ethoxymethyl, 2-methoxyethyl, 2-ethoxyethyl, 2-n-propoxyethyl, cyclopropyl, cyclobutyl, cyclopentyl or cyclohexyl.

8. The compound of claim 1, wherein $R^c$ is methyl, ethyl, n-propyl, isopropyl, t-butyl, cyclopropyl, cyclobutyl, cyclopentyl or cyclohexyl.

9. A compound having one of the following structures:

(1)

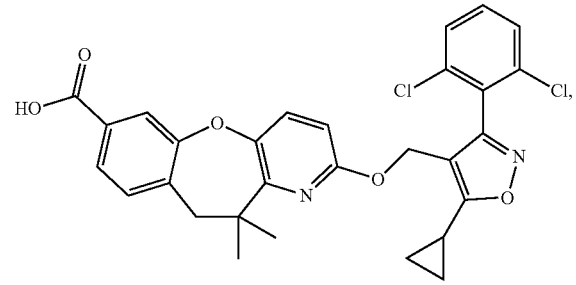

(2)

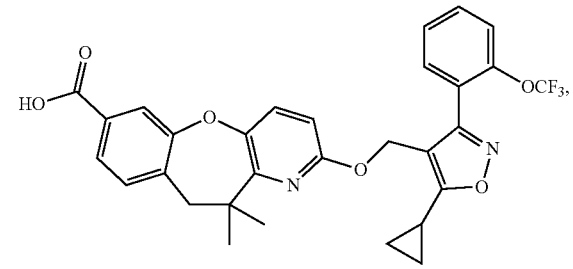

(3)

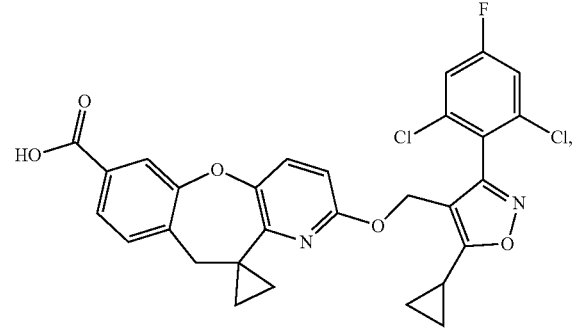

(4)

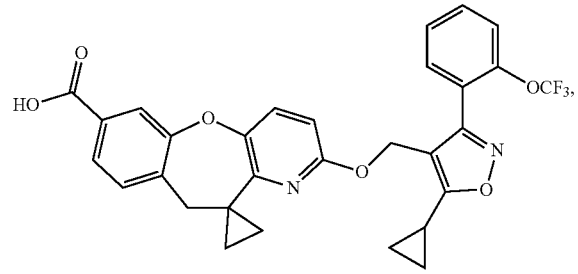

-continued
(5)
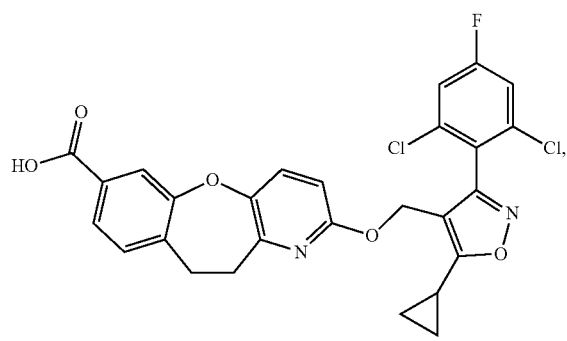
(6)
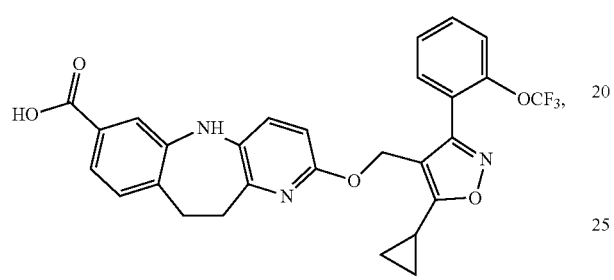
(8)
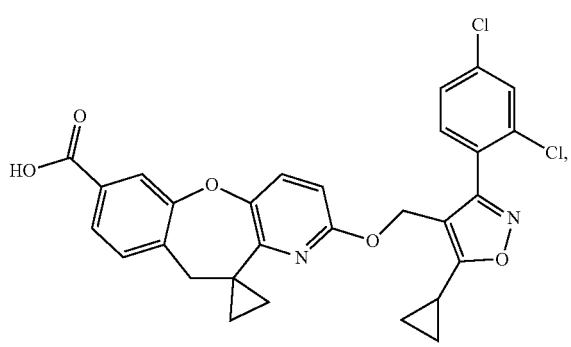
-continued
(9)
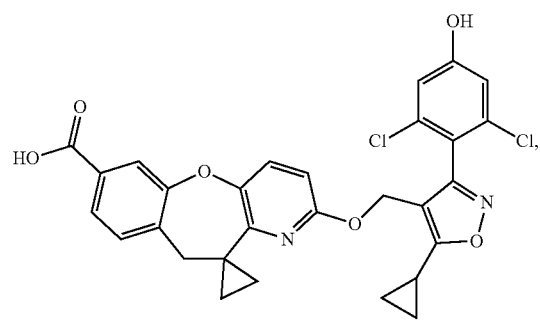
(10)
or a stereoisomer, a geometric isomer, a tautomer, an N-oxide, or a pharmaceutically acceptable salt thereof.
10. A pharmaceutical composition comprising the compound of claim 1, and a pharmaceutically acceptable carrier, excipient, diluent, adjuvant, medium or a combination thereof.
* * * * *